United States Patent
Shibuya et al.

(10) Patent No.: US 12,091,700 B2
(45) Date of Patent: Sep. 17, 2024

(54) METHOD AND APPARATUS FOR SCREENING OF CELL STRAINS AND CULTURE CONDITIONS

(71) Applicant: HITACHI, LTD., Tokyo (JP)

(72) Inventors: Keisuke Shibuya, Tokyo (JP); Kenichirou Oka, Tokyo (JP); Takeyuki Kondou, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1048 days.

(21) Appl. No.: 16/771,837

(22) PCT Filed: Nov. 1, 2018

(86) PCT No.: PCT/JP2018/040709
§ 371 (c)(1),
(2) Date: Jun. 11, 2020

(87) PCT Pub. No.: WO2019/116772
PCT Pub. Date: Jun. 20, 2019

(65) Prior Publication Data
US 2021/0189452 A1    Jun. 24, 2021

(30) Foreign Application Priority Data

Dec. 12, 2017 (JP) .................. 2017-238091

(51) Int. Cl.
C12Q 1/02    (2006.01)
C12M 1/34    (2006.01)

(52) U.S. Cl.
CPC ............ *C12Q 1/02* (2013.01); *C12M 41/32* (2013.01)

(58) Field of Classification Search
CPC ......... C12Q 1/02; C12M 41/32; C12M 41/46; C12M 41/48; G01N 33/5005; G01N 33/5038
See application file for complete search history.

(56) References Cited

U.S. PATENT DOCUMENTS

| | | |
|---|---|---|
| 2007/0231895 A1 | 10/2007 | Lee et al. |
| 2010/0081122 A1 | 4/2010 | Shibuya et al. |
| 2014/0017706 A1 | 1/2014 | Freitas et al. |
| 2017/0017891 A1 | 1/2017 | Thompson et al. |

FOREIGN PATENT DOCUMENTS

| | | |
|---|---|---|
| JP | 2005-506840 A | 3/2005 |
| JP | 2008-178344 A | 8/2008 |
| JP | 2009-514532 A | 4/2009 |
| JP | 2009-232861 A | 10/2009 |
| JP | 2010-81809 A | 4/2010 |
| JP | 2013-85516 A | 5/2013 |
| JP | 2014-503220 A | 2/2014 |
| JP | 2017-511688 A | 4/2017 |
| JP | 2019-4723 A | 1/2019 |
| WO | 03/029425 A2 | 4/2003 |
| WO | 2007/056062 A2 | 5/2007 |
| WO | 2016/193083 A1 | 12/2016 |
| WO | 2018/235441 A1 | 12/2018 |

OTHER PUBLICATIONS

Gramer et al. "A semi-empirical mathematical model useful for describing the relationship between carbon dioxide, pH, lactate and base in a bicarbonate-buffered cell-culture process" Biotechnol. Appl. Biochem. (2007) 47, 197-204 (Year: 2007).*
Japanese Office Action received in corresponding Japanese Application No. 2017-238091 dated Mar. 29, 2022.
Mugdha Gadgil, "Development of a mathematical model for animal cell culture without pH control and its application for evaluation of clone screening out comes in shake flask culture", Journal of Chemical Technology & Biotechnology, vol. 90, 2015, pp. 166-175.
International Search Report of PCT/JP2018/040709 dated Feb. 5, 2019.
Japanese Office Action received in corresponding Japanese Application No. 2017-238091 dated Sep. 13, 2022.

* cited by examiner

*Primary Examiner* — Thane Underdahl
(74) *Attorney, Agent, or Firm* — MATTINGLY & MALUR, PC

(57) ABSTRACT

A method and apparatus for screening of cell lines and culture conditions includes a target value setting step that sets a target value relating to a metabolic reaction of a culture cell; a first culturing step; an analysis step; an analysis value calculation step that performs a metabolism analysis based on an analysis result from the analysis step and calculates an analysis value; a culture condition computation step that computes, using a correlation model, a culture condition giving an analysis value most close to the target value, and modifies the culture condition set in the first culturing step to the computed culture condition; a second culturing step that cultures a cell under the modified culture condition; and a screening step.

4 Claims, 17 Drawing Sheets

METHOD AND APPARATUS FOR SCREENING OF CELL STRAINS AND CULTURE CONDITIONS

TECHNICAL FIELD

The present invention relates to a method and apparatus for screening of cell lines and culture conditions.

BACKGROUND ART

Some useful substances are produced in trace amounts in the natural world by the biological activities of cells such as microorganisms, animal cells, and plant cells. Such useful substances can be manufactured in large amounts by the application of synthetic biology. The high-volume manufacture of the useful substances manufactures a target useful substance (herein also referred to as an "objective substance") by culturing a cell that produces the objective substance in an appropriate culture environment, and recovering the produced objective substance typically by purification. Such objective substances, which have been manufactured using cells, are applied to industrial fields represented by foodstuffs and beverages, chemicals and fibers, pharmaceutical preparations, cosmetics, toiletries, and energy, and to research support fields (such as devices and reagents for research, and DNA synthesis) which support the industrial fields.

To construct a manufacturing process for high-volume production of such an objective substance, a molecular biological approach as a synthetic biological technique creates a novel cell line that allows high-efficiency production, or artificially constructs a metabolic system. Assume that cell screening finds a cell that produces a novel secondary metabolite. In this case, a gene cluster producing the compound (secondary metabolite) is discovered, the functions of genes in the cluster are revealed, and the cell receives gene recombination for higher productivity. Specifically, a cycle of: (1) discovery→(2) analysis→(3) design→(4) gene recombination→(5) testing→(6) learning→(3) design→ . . . repeats. Thereafter, a manufacturing process is constructed for the selected cell line candidate by optimizing a culturing system, a culture condition, and other factors.

Such culturing systems for cell culture are classified into batch culture, feeding culture (or semi-batch culture), and continuous culture (or perfusion culture).

The batch culture is a culturing system that prepares a fresh medium for each culture, inoculates a cell line into the medium, and adds no other medium until harvesting. The batch culture features dispersion or reduction of contamination risk, although having a culture-to-culture variation in quality.

The feeding culture is a culturing system that adds another portion of the medium or a specific ingredient in the medium to the culture, but does not extract a product until the completion of culture.

The continuous culture is a culturing system that feeds the medium successively to the culture system and simultaneously extracts a culture in the same amount with the fed medium. The continuous culture features stable productivity because of a stably holdable culture environment.

The manufacturing process construction determines culture conditions, such as temperature and dissolved oxygen concentration, that provide higher productivity of the culturing system. However, the synthesis mechanism of a useful substance in cells is very complicated and has not been sufficiently clarified. A conventional screening for an appropriate culture condition has to grasp the state of a culture cell which affects the productivity and/or quality, to grasp the causation between the culture condition and the cell state, and to explore such a culture condition to optimize the productivity and quality. Thus, the conventional screening for an appropriate culture condition is performed by trial and error in which cells are actually cultured under various culture conditions. There are a large number of parameters of a culture environment to be studied, such as temperature, pH, and dissolved oxygen concentration. When conditions are modified for the parameters, the number of conditions for the culture environment exponentially increases as a result of combinations of the parameters. Accordingly, the manufacturing process construction needs a very large number of culture experiments and needs huge time and cost to perform screening of culture conditions.

An exemplary method for selecting a cell line candidate is proposed in Patent Literature 1. Patent Literature 1 describes a method for whole cell engineering of new and modified phenotypes using real-time metabolic flux analysis. The method includes the steps of (a) making a modified cell by modifying the genetic composition of a cell; (b) culturing the modified cell to generate a plurality of modified cells; (c) measuring at least one metabolic parameter of the cell by monitoring the cell culture of step (b) in real time; and (d) analyzing the data of step (c) to determine if the measured parameter differs from a comparable measurement in an unmodified cell under similar conditions, thereby identifying an engineered phenotype in the cell using real-time metabolic flux analysis.

CITATION LIST

Patent Literature

Patent Literature 1: Japanese Unexamined Patent Application Publication (JP-A) (Translation of PCT Application) No. 2005-506840

SUMMARY OF INVENTION

Technical Problem

The method described in Patent Literature 1 allows efficient selection of a modified cell. However, there is a very large number of conditions in the culture environment, and this requires a very large number of culture experiments for the manufacturing process construction. The screening of culture conditions still needs huge time and cost even according to this method. Specifically, the method described in Patent Literature 1 fails to screen for an optimal culture condition.

The present invention has been made under these circumstances and has an object to provide a method and apparatus each of which allows easy screening of cell lines and culture conditions.

Solution to Problem

After intensive investigations to achieve the object, the inventors of the present invention have found that the following technique realizes an intracellular metabolic reaction close to the purpose, and allows the production of an objective substance with stable quality and high productivity. Specifically, a target intracellular metabolic reaction is set, and a correlation model between culture conditions (culture environmental factors such as temperature and pH) and rates of metabolic reactions is constructed in a cell to be used. Using the correlation model, a culture condition most close to the set intracellular metabolic reaction model (namely, the target value) is computed, and this actualizes an intracellular metabolic reaction close to the target. The inventors have found that this enables the objective substance to form with high productivity and stable quality. The present invention has been made on the basis of these findings. As used herein, the term "correlation model" refers to a model that expresses a correlation among a metabolic reaction, an metabolic rate formula relating to the metabolic reaction, and a culture environmental factor affecting the metabolic reaction and/or the metabolic rate formula. Namely, the correlation model has metabolic rate formulae in a number corresponding to the number of the identified metabolic reactions.

The object according to the present invention is achieved by the following means.

A method according to the present invention for screening of cell lines and culture conditions includes a target value setting step, a first culturing step, an analysis step, an analysis value calculation step, a culture condition computation step, a second culturing step, and a screening step. The target value setting step sets a target value relating to a metabolic reaction of a culture cell. The first culturing step cultures the culture cell under a preset culture condition. The analysis step analyzes a culture (culture medium) including the cultured cell. The analysis value calculation step performs a metabolism analysis on the basis of an analysis result from the analysis step, to determine analysis values by calculation. The culture condition computation step computes, using a correlation model, a culture condition giving an analysis value, among the analysis values, most close to the target value, and modifying the culture condition set in the first culturing step into the computed culture condition. The second culturing step cultures a cell belonging to the same cell line as with the culture cell, where the culture works under the modified culture condition, and sends a resulting culture to the analysis step. The method performs a series of the steps from the analysis step to the second culturing step on different culture cells and different culture conditions, to give analysis values. The screening step screens for a cell line and a culture condition each of which gives an analysis value, among the analysis values, most close to the target value.

An apparatus according to the present invention for screening of cell lines and culture conditions includes a target value setter, a culturing device, an analyzer, an analysis value calculator, a culture condition computer, and a screener. The target value setter sets a target value relating to a metabolic reaction of a culture cell. The culturing device cultures the culture cell under the set, or modified, culture condition. The analyzer analyzes a culture including the culture cell cultured in the culturing device. The analysis value calculator performs a metabolism analysis on the basis of an analysis result from the analyzer and determines analysis values by calculation. The culture condition computer computes, using a correlation model, a culture condition giving an analysis value, among the analysis values, most close to the target value, and modifies the culture condition set in the culturing device into the computed culture condition. The screener screens for a cell line and a culture condition each of which gives an analysis value most close to the target value, where the analysis value is selected from among analysis values obtained by cultures on different culture cells and different culture conditions.

Advantageous Effects of Invention

The present invention can provide a method and apparatus for screening of cell lines and culture conditions, each of which allows easy screening for a cell line and a culture condition.

DESCRIPTION OF EMBODIMENTS

A method and apparatus according to one embodiment of the present invention for screening of cell lines and culture conditions (hereinafter simply referred respectively to a "screening method" and a "screening apparatus") will be illustrated in detail below, with reference to the attached drawings as appropriate. In the following description, characteristic properties of a cell line necessary in the production of an objective substance will be initially illustrated, and subsequently, the construction of a correlation model between culture conditions and metabolic reaction rates will be illustrated, followed sequentially by illustration of embodiments or forms of the screening apparatus, and embodiments or forms of the screening method.

Figure 1:
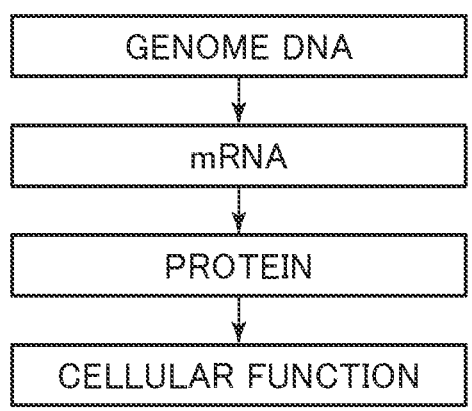
FIG. 1 is a flow chart illustrating transfer and expression of genetic information and exertion of a cellular function.
Figure 2:
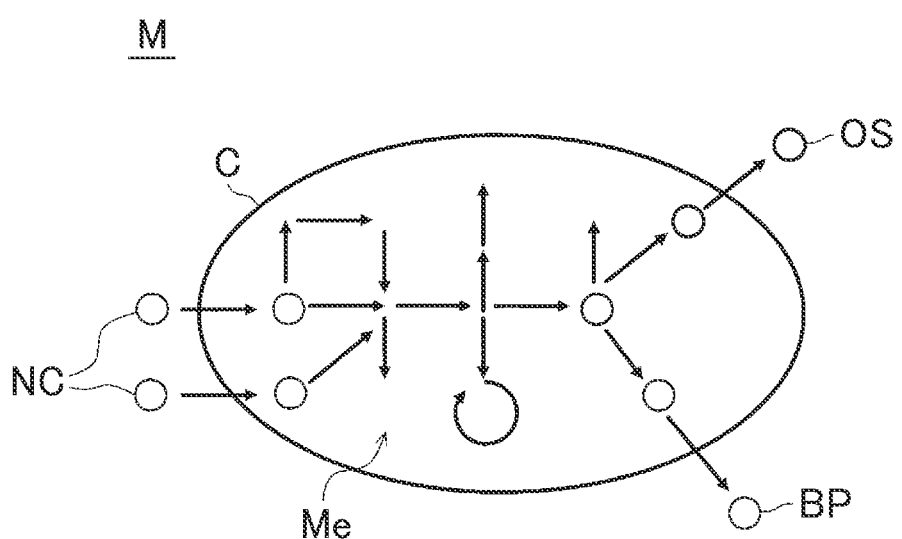
FIG. 2 conceptually illustrates a cell line that produces an objective substance by intracellular metabolism.
Figure 3A:
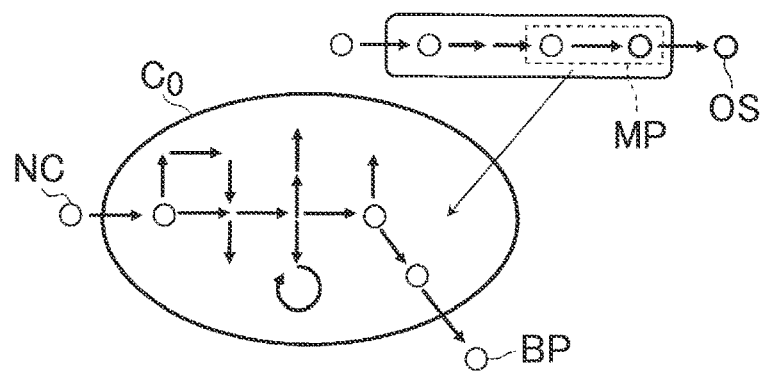
FIG. 3A conceptually illustrates exemplary intracellular metabolism before gene recombination.
Figure 3B:
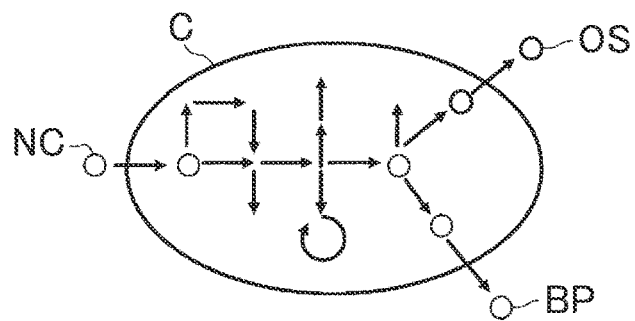
FIG. 3B conceptually illustrates exemplary intracellular metabolism after gene recombination.
Figure 3C:
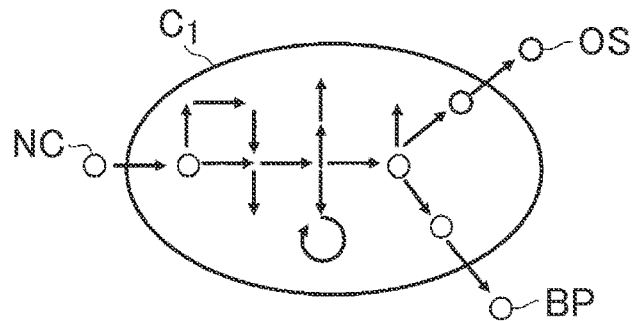
FIG. 3C conceptually illustrates other exemplary intracellular metabolism before gene recombination.
Figure 3D:
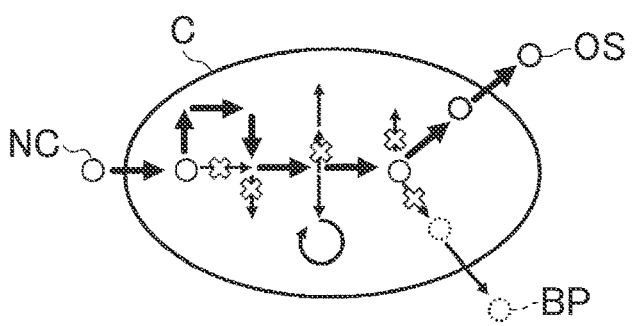
FIG. 3D conceptually illustrates other exemplary intracellular metabolism after gene recombination.

1. Characteristic Properties of Cell Line Necessary in Production of Objective Substance FIG. 1 is a flow chart illustrating transfer and expression of genetic information (central dogma), and subsequent exertion of a cellular function. FIG. 2 conceptually illustrates a cell line that produces an objective substance by intracellular metabolism. FIG. 3A conceptually illustrates an exemplary intracellular metabolism before gene recombination. FIG. 3B conceptually illustrates an exemplary intracellular metabolism after gene recombination. FIG. 3C conceptually illustrates another exemplary intracellular metabolism before gene recombination. FIG. 3D conceptually illustrates another exemplary intracellular metabolism after gene recombination.

A cell takes in a material that will work as a nutritional component, and produces an objective substance by synthesis and modification in its intracellular metabolic pathway. The production efficiency of the objective substance depends on the rate of a metabolic reaction, which is one of cellular functions, and the metabolic reaction rate depends on culture conditions. The production of such a substance needs expression of an enzyme protein in all or entire metabolic pathways, where the enzyme protein promotes the intracellular metabolic reaction. The flow in which the enzyme protein is expressed and works as a cellular function will be illustrated below, with reference to FIG. 1. A genome DNA in the cell encodes the gene of the enzyme protein. The genome DNA gives a mRNA by transcription, the mRNA gives a protein such as the enzyme protein by translation. This gives the enzyme protein by expression. The enzyme protein, which is expressed in the above manner, is activated typically through the formation of a higher order structure or modification, works as a cellular function, and increases the metabolic reaction rate. Factors involved in activities and metabolic reactions of the mRNA and the enzyme protein depend on culture conditions. The metabolic reaction rates and substance production productivity also depend on the culture conditions. The transcript level, kinetics, and other factors in a process from genome DNA to mRNA can be understood through transcriptome analysis. The expression level, kinetics, and other factors of the protein expressed from genome DNA or mRNA can be understood through proteome analysis.

FIG. 2 illustrates the flow in which the cell takes in the material, which will work as a nutritional component, and produces the objective substance by synthesis and/or modification in the intracellular metabolic pathway. As illustrated in FIG. 2, the objective substance OS is produced by an objective substance-producing cell C from a material nutritional component NC in a culture M through a metabolism Me (synthetic reaction) in the cell C. The objective substance OS production may also produce a by-product BP. The arrows ("→") in FIG. 1 indicate the metabolic pathway.

Non-limiting examples of the cell C usable in the embodiment include Chinese hamster ovary cells (CHO cells), baby hamster kidney cells, and murine myeloma cells. The cell C, when being an adhesive cell, can undergo spinner culture by allowing the cell to attach to a carrier such as a microcarrier and to suspend in a medium (culture medium). Non-limiting examples of the cell C usable in the embodiment include not only cells derived from animals, but also plant cells, photosynthetic bacteria, microalgae, blue-green algae, insect cells, bacteria, yeast, fungi, algae, and *Escherichia coli*. The embodiment can employ any cell capable of producing the objective substance OS, without limitations to the above-mentioned cells.

Non-limiting examples of the objective substance OS include bioactive substances, represented by antibodies. The category antibodies includes monoclonal antibodies, polyclonal antibodies, humanized antibodies, human antibodies, and immunoglobulins. The bioactive substances are not limited to antibodies, but also include biopharmaceuticals such as tissue-type plasminogen activators, which are used as thrombolytic agents, erythropoietin, and interferons; as well as other industrially useful proteins, and proteins combined with any of carotenoids such as p-carotene and astaxanthin, and colorants such as chlorophyll and bacteriochlorophyll. Non-limiting examples of the objective substance OS also include phycobilin proteins such as phycocyanine, which are used typically for coloring of foodstuffs, cosmetics, and toiletries. The medium for use in the culture is not limited and can be any conventional medium that is effective for the proliferation of the cell C, which is a culture subject, and for the production of the objective substance OS. The objective substance OS may be not only a protein, but also a secondary metabolite such as an antibiotic, and can be any substance that is produced by metabolism in the cell C.

The cell C often receives gene recombination for higher productivity of the objective substance OS. The gene recombination is designed to increase the productivity of the objective substance by adding, to the cell C, a metabolic pathway necessary for the synthesis of the objective substance OS, and/or by increasing or decreasing the reaction rate of a metabolic pathway of an original cell line (such as a natural cell line). The term "natural cell line" in the embodiment refers to a cell line which does not undergo gene recombination to introduce a gene that produces the objective substance, and specifically refers to a cell line that is isolated (cloned) from the natural world or a living body typically by limiting dilution. The gene recombination regulates the metabolic reaction rate by increasing or decreasing an enzyme protein or another material involved in the metabolic reaction.

An exemplary gene recombination introduces a gene derived from another cell and relating to the metabolic pathway MP that produces the objective substance OS (such as an enzyme protein gene) into a cell $C_0$ that does not produce the objective substance OS, as illustrated in FIG. 3A. This allows the resulting cell C, which is formed by gene recombination and can produce the objective substance OS, to be modified in its intracellular metabolism and to produce the objective substance OS from the nutritional component NC, as illustrated in FIG. 3B.

Another exemplary gene recombination deletes a gene involved in a poorly efficient metabolic pathway from a cell $C_1$ capable of producing the objective substance OS as illustrated in FIG. 3C, or introduces, to the cell $C_1$, a gene to produce a substance inhibiting the metabolic pathway, as illustrated in FIG. 3D. This inhibits such a poorly efficient metabolic pathway or pathways as illustrated in FIG. 3D, and can give a cell C that has higher capability of producing the objective substance OS from the nutritional component NC. The bold arrows in FIG. 3D indicate that the productivity increases. The open cross marks "×" in metabolic pathways in FIG. 3D indicate that the metabolic pathways are inhibited. The circles shown by dashed lines in FIG. 3D indicate that the by-product BP, which has been produced, is inhibited and not produced, or is produced in a smaller amount.

Each metabolic reaction rate in the cell during culture may depend also on culture environmental factors such as temperature, pH, dissolved oxygen, dissolved carbon dioxide, bubbles formed by submerged bubbling, and shear stress by agitation. This is because the culture environment factors affect the activities typically of enzyme proteins and coenzymes expressed in the cell C.

It is therefore believed that a cell line necessary for the production of the objective substance OS requires the following two characteristic properties.

(1) The cell line has appropriate metabolic pathways (metabolic pathways which are just enough) capable of producing the objective substance OS.

(2) In each metabolic pathway, the activity of an enzyme protein that promotes the reaction, or the activity of an inhibitory factor that inhibits the reaction, is optimized in the entire metabolic pathway.

The characteristic property (1) can be achieved by gene recombination and/or genome editing as described above, and the characteristic property (2) can be achieved by optimizing culture conditions. The term "genome editing" refers to a technique of modifying (cleaving and editing) an optional gene on the genome.

The high-volume production of the objective substance OS significantly has to optimize the characteristic properties (1) and (2) simultaneously. This is advantageously achieved probably by grasping how intracellular metabolic reactions correlate with culture conditions (culture environmental factors), and formularizing (modeling) the correlation between metabolic reaction rates and culture environmental factors, on each of cell line candidates which have undergone gene recombination and/or genome editing. Thus, correlation models modeled in the above manner are constructed on the cell lines, and productivities of the correlation models under the optimized culture condition are compared. This can provide an optimal combination of a cell line and a culture condition.

Figure 4:
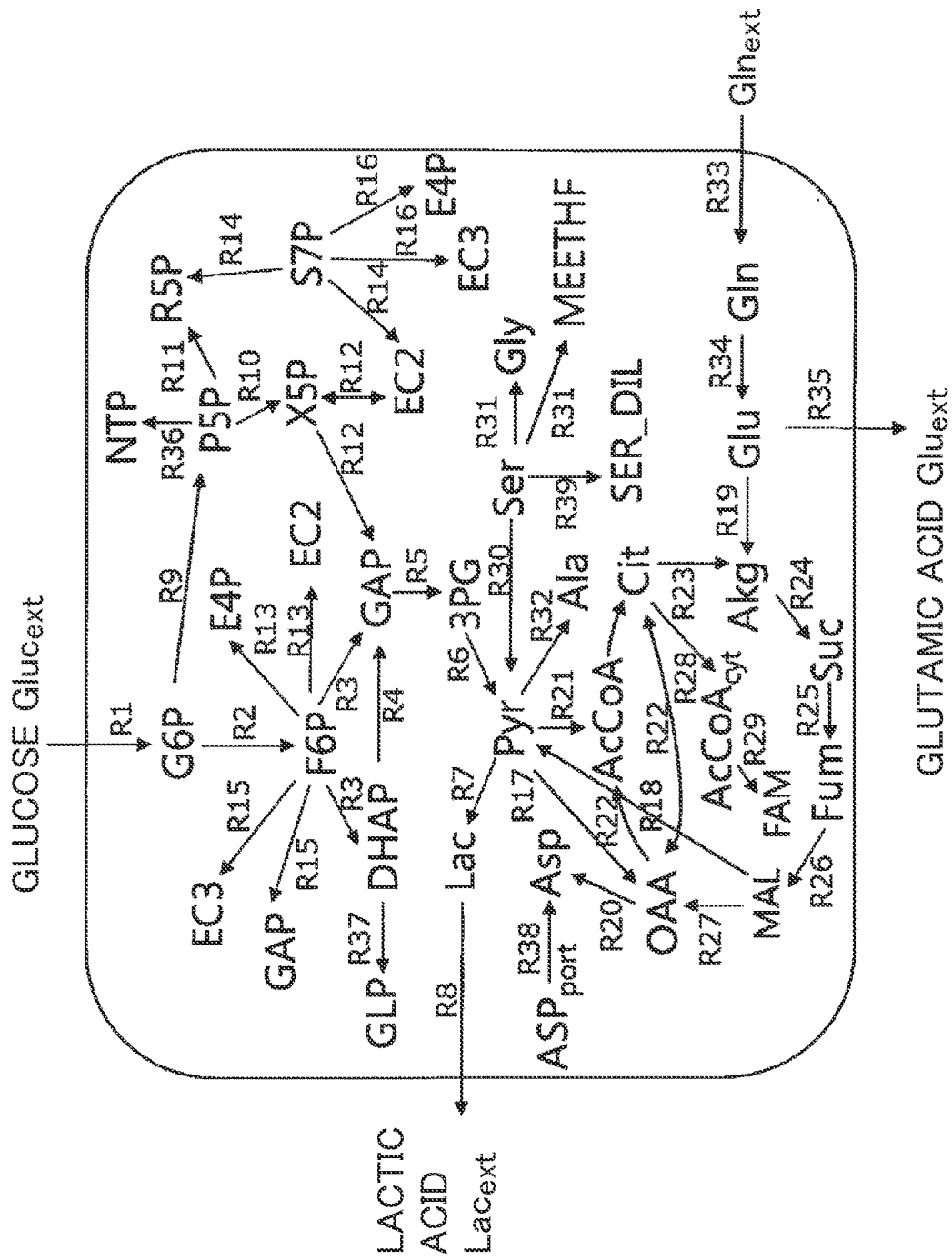
FIG. 4 illustrates a part of metabolic pathways of a Chinese hamster ovary (CHO) cell.

2. Construction of Correlation Model between Culture Condition and Metabolic Reaction Rate FIG. 4 illustrates a part of metabolic pathways of a Chinese Hamster Ovary (CHO) cell. The CHO cell is one of cells frequently used in manufacturing of antibody preparations.

An objective substance OS is produced according to the metabolic pathways as illustrated in FIG. 4. For higher production efficiency of the objective substance OS, it is basically desirable that the metabolic pathway from the material nutritional component NC to the objective substance OS has a high metabolic reaction rate, and a branch metabolic pathway (by-product BP) has a low metabolic reaction rate.

The reaction numbers (such as R1) and metabolic reaction formulae in the metabolic pathways of the CHO cell in FIG. 4 are as follows. The symbol "=" in the following illustration indicates reversible or irreversible metabolism mainly by the action of an enzyme protein.

Reaction Numbers and Metabolic Reaction Formulae in FIG. 4

Reaction Number: Metabolic Reaction Formula $Gluc_{ext}=G6P$      R1

$G6P=F6P$      R2

$F6P=DHAP+GAP$      R3

$DHAP=GAP$      R4

$GAP=3PG$      R5

$3PG=Pyr$      R6

$Pyr=Lac$      R7

$Lac=Lac_{ext}$      R8

$G6P=P5P+CO2$      R9

$P5P=X5P$      R10

$P5P=R5P$      R11

$X5P=EC2+GAP$      R12

$F6P=EC2+E4P$      R13

$S7P=EC2+R5P$      R14

$F6P=EC3+GAP$      R15

$S7P=EC3+E4P$      R16

$Pyr+CO2=OAA$      R17

$MAL=Pyr+CO2$      R18

$Glu=Akg$      R19

$OAA=Asp$      R20

$Pyr=AcCoA+CO2$      R21

$OAA+AcCoA=Cit$      R22

$Cit=Akg+CO2$      R23

$Akg=0.5Suc+0.5Suc+CO2$      R24

$Suc=Fum$      R25

$Fum=MAL$      R26

$MAL=OAA$      R27

$Cit=OAA+AcCoA_{Cyt}$      R28

$AcCoA_{Cyt}=FAM$      R29

$Ser=Pyr$      R30

$Ser=Gly+\text{MEETHF}$      R31

$Pyr=Ala$      R32

$Gln_{ext}=Gln$      R33

$Gln=Glu$      R34

$Glu=Glu_{ext}$      R35

$P5P=NTP$      R36

$DHAP=GLP$      R37

$ASP_{prot}=Asp$      R38

$Ser=SER\_DIL$      R39

The abbreviations in FIG. 4 are as follows.
Abbreviations in FIG. 4
Gluc: Glucose
G6P: Glucose-6-phosphate
F6P: Fructose-6-phosphate
DHAP: Dihydroxyacetone phosphate
GAP: Glyceraldehyde-3-phosphate
3PG: 3-Phosphoglycerate
Pyr: Pyruvate
Lac: Lactic acid
P5P: Pyridoxyl-5-phosphate
X5P: Xylulose-5-phosphate
R5P: Ribose-5-phosphate
EC2: 2 enzyme-bound carbons
CO2: Carbon dioxide
E4P: Erythrose-4-phosphate
OAA: Oxaloacetate
S7P: Sedoheptulose-7-phosphate
MAL: Malate
Akg: α-Ketoglutarate
Asp: Aspartic acid
$ASP_{prot}$: Aspartic acid protein
AcCoA: Acetyl-CoA
$AcCoA_{Cyt}$: Acetyl-CoA cytosol
FAM: Fatty acid metabolism
Cit: Citric acid
Suc: Succinate
Fum: Fumarate
Ser: Serine
SER_DIL: Serine dilution
Gly: Glycine
MEETHF: Methylenetetrahydrofolate
Ala: Alanine
Gln: Glutamine
$Gln_{ext}$: External Glutamine
Glu: Glutamic acid
$Glu_{ext}$: External Glutamic acid
NTP: Nucleoside tri-phosphate (nucleoside triphosphate)
GLP: Glycerophosphate (glycerol 3-phosphate)

The metabolic reaction formulae relating to the metabolic pathways illustrated in FIG. 4 vary depending on culture conditions (culture environmental factors such as temperature (Tem), pH, dissolved oxygen (DO), dissolved carbon dioxide, bubbles formed by submerged bubbling, and shear stress caused by agitation). This requires knowledge about which culture environmental factor affects an individual metabolic reaction rate. The influence of such a culture condition can be reflected by publicly available documents and findings, such as papers (articles), journals, books, and experiment data; as well as experimentally obtained conditions. Specifically, the reaction numbers and metabolic reaction formulae, as well as already-published findings can be indicated as correlations, and on the basis of the correlations, the metabolic reaction rates can be expressed as functions of culture environmental factors. Examples of these will be described below.

Examples of Correlation Among Reaction Number and Metabolic Reaction Formula, and Already-Published Findings The correlations can be expressed typically as:

$R1 \propto DO, Tem$ (documents $a$ and $b$), $R2 \propto Tem$ (document $c$), $R3 \propto pH, DO$ (documents $d$ and $e$),

..., $R53 \propto pH, Tem$ (documents $f$ and $g$)

wherein DO represents the dissolved oxygen concentration;
and Tem represents the temperature.

Specifically, the documents a and b teach that the reaction number R1 has a correlation with DO and Tem; the document c teaches that the reaction number R2 has a correlation with Tem; the documents d, e teach that the reaction number R3 has a correlation with pH and DO; and the documents f and g teach that the reaction number R53 has a correlation with pH and Tem.

Examples of Metabolic Reaction Rate Expressed by Function of Culture Environmental Factor On the basis of the correlations, the metabolic reaction rates can be expressed by functions of the culture environmental factors. Such metabolic reaction rates expressed by functions of the culture environmental factors are expressed typically as follows:

$fR1(pH, DO, Tem...)$, $fR2(pH, DO, Tem...)$, $fR3(pH, DO, Tem...)$,

...

$fR53(pH, DO, Tem...)$.

In the embodiment, culturing works multiple times with varying settings, as described later. Of course, in each culture, an identical condition is applied to the culture environmental factors such as pH, DO, and Tem in the functions fR1 ... fR53.

From the metabolic reaction rates and the material balance, the nutrient substrate consumption rate and the production rate of the objective substance under the set culture condition can be estimated.

However, the correlations and the functions (correlation model) vary from a cell to another, and information from already known findings may be insufficient.

In the embodiment, therefore, a cell to be used is cultured under a specific culture condition and receives metabolism analysis, as described later. The culture experimental data are compared with data according to the correlation model. When the two disagree with each other, the parameter(s) of the correlation model is corrected to approximate to the culture experimental data. Using the correlation model after the correction, a culture condition under which the target value (such as targeted metabolic reaction rate) is obtained is computed. The cell is cultured under the culture condition determined by computation, and the metabolic reaction rate in the culture is compared with the computed reaction rate. When the two disagree with each other, the parameter(s) of the correlation model is corrected again.

By repeating a series of the operations, the experimental metabolic reaction rate approaches and then agrees with the computed metabolic reaction rate. The correlation model in which the experimental metabolic reaction rate agrees with the computed metabolic reaction rate has high precision and, simultaneously, gives an optimal culture condition. As used herein, the term "agree with" means and includes not only that two numerical values or other data to be compared are identical, but also that the two data may probably fall within such a range as to give equivalent advantageous effects. The range that probably gives equivalent advantageous effects may typically be the range of the target value ±20%, and more preferably the target value ±10%, although the range is not limited to these and can be optionally set.

As described above, the embodiment can provide an optimal culture condition more reliably and more stably through the operations as above and can significantly reduce the number of culture experiments, as compared with conventional techniques which work on empirical rules. When including two or more culturing devices 3 as described later (see culture vessels 37a to 37h in FIG. 9), the screening method according to the embodiment can evaluate a number of culture conditions at once. This allows screening for an optimal culture condition in a short time as compared with the conventional techniques.

3. Embodiment of Screening Apparatus

Figure 5:
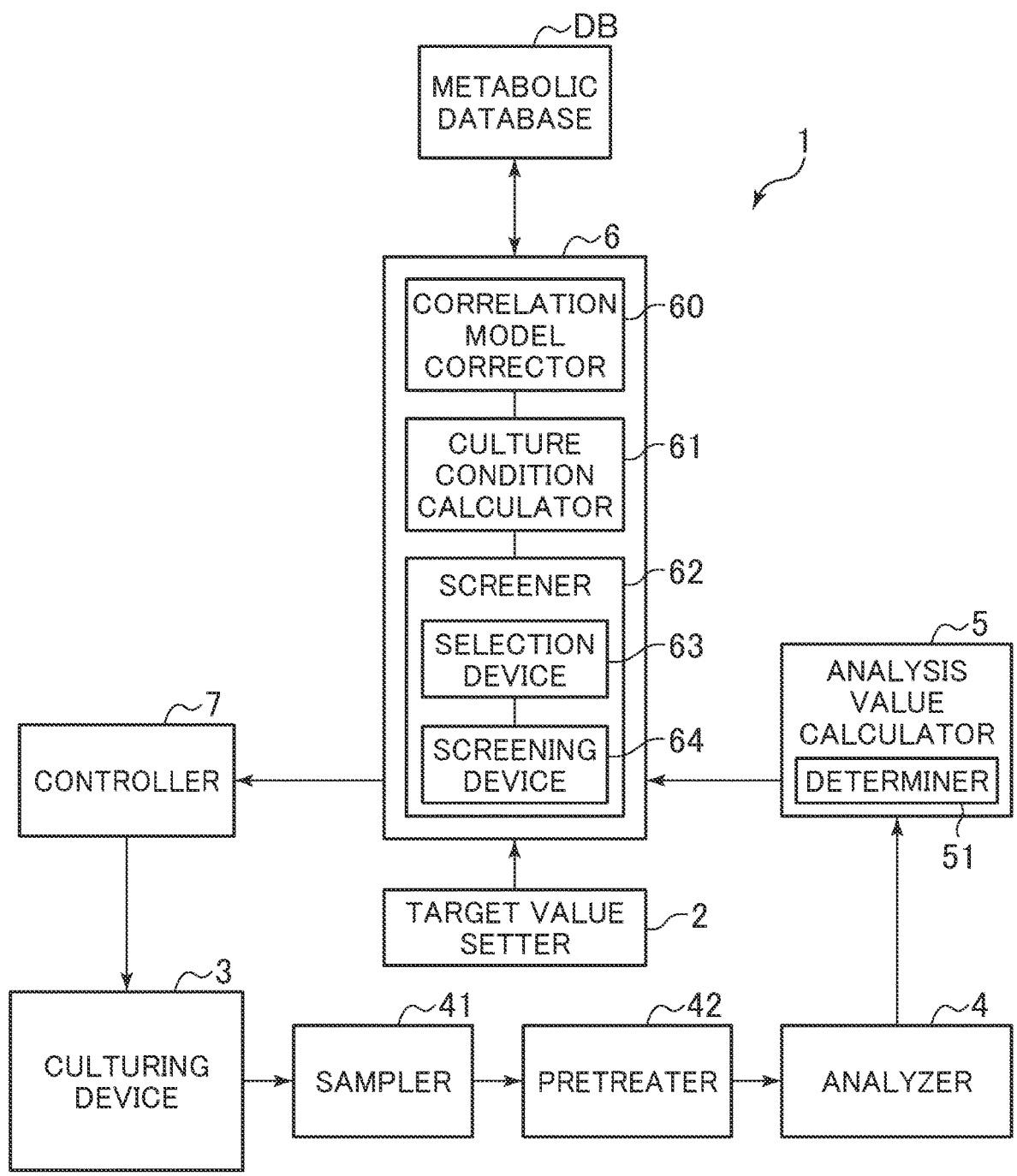
FIG. 5 is a schematic diagram of an exemplary apparatus according to the embodiment for screening of cell lines and culture conditions.

FIG. 5 schematically illustrates one example of a screening apparatus according to the embodiment.

As illustrated in FIG. 5, the screening apparatus 1 includes a target value setter 2, a culturing device 3, an analyzer 4, an analysis value calculator 5, a culture condition computer 61, and a screener 62. The screening apparatus 1 also includes a controller 7 and a metabolic database DB. These devices or means will be described below.

Target Value Setter 2

The target value setter 2 is a device to set a target value relating to a metabolic reaction of a cell to be cultured (culture cell). The target value setter 2 includes an input device and an output device (each not shown). The input device is a device to input a target value relating to a targeted metabolic reaction, to efficiently produce an objective substance. Non-limiting examples of the input device include a keyboard and a mouse for data input. The input data is stored in a storage device, such as a hard disk drive, provided in the culture condition computer 61 shown in FIG. 5. The output device displays information, such as the input value input by the input device, for visual recognition. Non-limiting examples of the output device include a monitor; and a device (printer) that outputs information to a paper medium.

The target value can be any one relating to a metabolic reaction of the culture cell, is not limited, but is exemplified typically by a metabolic pathway model or a metabolic reaction rate for the efficient production of the objective substance. The metabolic pathway model can for example be a model constructed typically on the basis of a biochemically identified or proposed metabolic pathway. Non-limiting examples of the metabolic pathway include glycolytic pathway, gluconeogenesis, citric acid cycle, glyoxylate cycle, oxidative phosphorylation, pentose phosphate cycle, reductive pentose phosphate cycle, urea cycle, beta-oxidation, amino acid biosynthesis, nucleotide metabolism, glycogenesis, lipid biosynthesis, fatty acid biosynthesis, cholesterol biosynthesis, purine biosynthetic pathway, pyrimidine biosynthetic pathway, and shikimic acid pathway.

Culturing Device 3

The culturing device 3 is a device (culture vessel) that cultures a culture cell under the set, or a modified, culture condition. The culturing device 3 performs a first culturing step S20 and a second culturing step S60 described later (see FIG. 12). The modified culture condition will be described later. Exemplary culturing methods which the culturing device 3 may employ are classified into three techniques, i.e., batch culture, feeding culture, and continuous culture. The batch culture is a culturing method in which a fresh medium is prepared for each culture, a cell line is inoculated in or on the prepared medium, and no other portion of medium is added until harvesting. The feeding culture is a culturing method in which another portion of the medium or a specific ingredient in the medium is added during culture, but the resulting product is not extracted until the completion of culture. The continuous culture is a culturing method in which the medium is continuously fed to the culture system, and simultaneously, a culture (culture solution) M is extracted in an amount equal to that of the fed medium. In any culturing method, non-limiting examples of the parameters (culture environmental factors) of the culture environment include temperature, pH, dissolved oxygen concentration (DO), dissolved carbon dioxide concentration ($DCO_2$), bubbles formed by submerged bubbling, and shear stress caused by agitation. Culture apparatuses for use in the culturing methods will be illustrated below.

i. Culture Apparatus for Batch Culture

Figure 6:
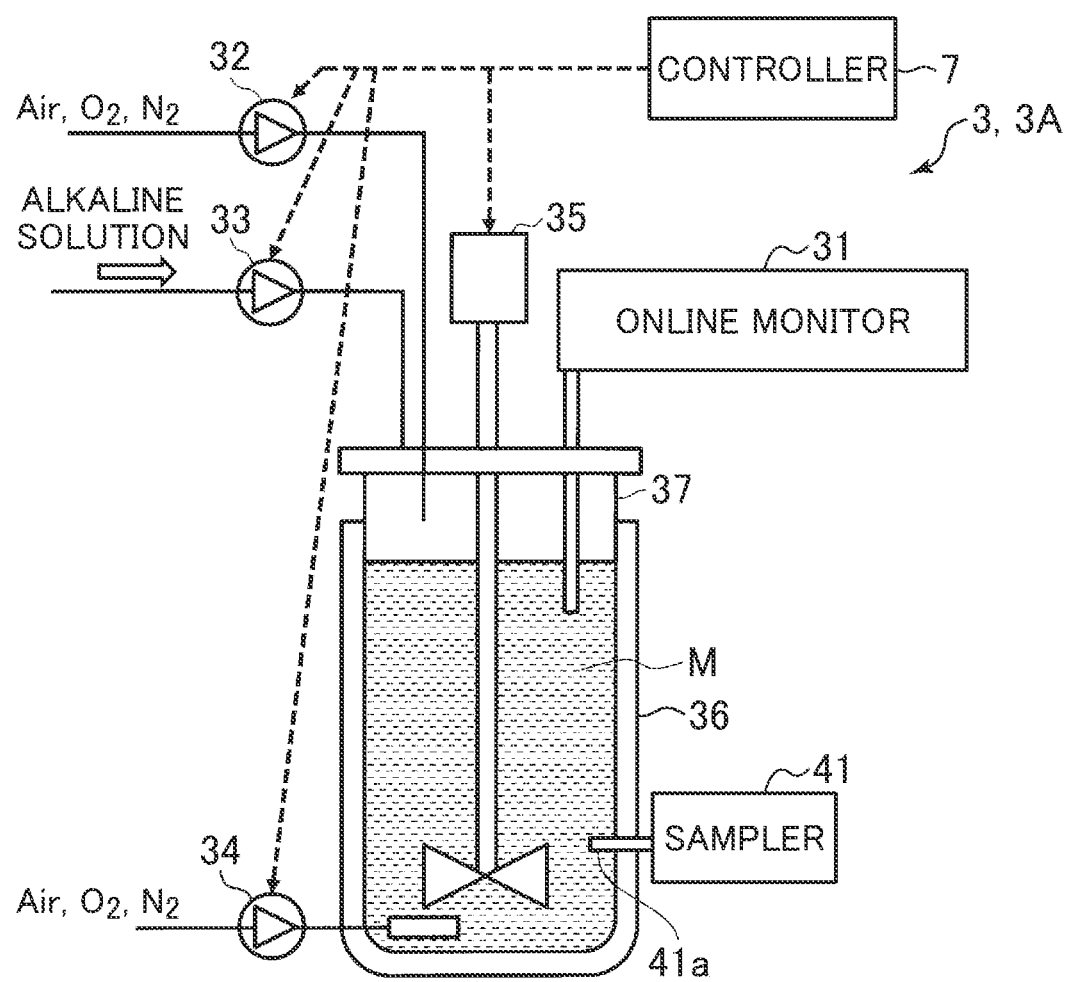
FIG. 6 is a schematic diagram of a culture apparatus according to a batch culture system.

FIG. 6 schematically illustrates a batch culture apparatus. As illustrated in FIG. 6, a batch culture apparatus 3A, which is an example of the culturing device 3, measures culture environmental factors, such as pH, DO, and temperature, of the culture M using an online monitor 31. The monitored culture environmental factors are each controlled on the basis of corresponding measurements by a controller 7 independently for each device (unit) such as a gas phase oxygen concentration regulator 32, a pH regulator 33, a dissolved oxygen concentration regulator 34, an agitator 35, or a temperature regulator 36. The control works, to allow each measured value to converge or approximate to a corresponding target value. How controller 7 controls a value to approximate to the corresponding target value in individual steps will be described below as a control flow.

(1) Each measuring device (online monitor 31) typically for the measurement of pH, DO, or temperature gives each measured value, where the measuring device is disposed in the culture vessel 37.

(2) The controller 7 determines whether each measured value agrees with a corresponding preset controlling value. Upon agreement, return to the step (1). Upon disagreement, go to the step (3).

(3) When the step (2) determines that the measured value disagrees with the controlling value, the controller 7 sends actuating signals independently to the devices 32 to 36 to change or modify the actuating variables so as to allow the measured value to converge or approximate to the controlling value. Non-limiting examples of the technique for controlling the devices 32 to 36 include known techniques such as ON/OFF control technique, proportional control technique, and proportional-integral-derivative (PID) control technique. After modifying the actuating variables, return to the step (1).

Non-limiting examples of the actuating variables for use herein in the devices 32 to 36 include following actuating variables (a) to (c):

(a) pH: Increase or decrease of the feed amount of carbon dioxide gas in a bubbling gas, and the injection volume of an acidic solution or alkaline solution.

(b) Dissolved oxygen concentration and gas phase oxygen concentration: Increase or decrease of the feed amount of oxygen in the bubbling gas, increase or decrease of the culture agitation rate, and increase or decrease of the culture vessel pressure.

(c) Temperature: When the temperature regulator 36 is a water jacket or another similar device, rise or fall of the fed water temperature, and increase or decrease of the cooling water feeding rate; when the temperature regulator 36 is a heating electric heater or another similar device, increase or decrease of the power supply for the heating electric heater; and when temperature regulator 36 employs heating steam, increase or decrease of the heating steam feed amount.

The steps (1) to (3) repeatedly work until a termination order of the screening method is given. The steps (1) to (3) may repeat at time intervals of from about 1 second to about 10 minutes, while the repetition intervals are appropriately determined on the basis of characteristic properties of the cell C to be cultured, and dynamic properties of the culturing device 3.

ii. Culture Apparatus for Feeding Culture

Figure 7:
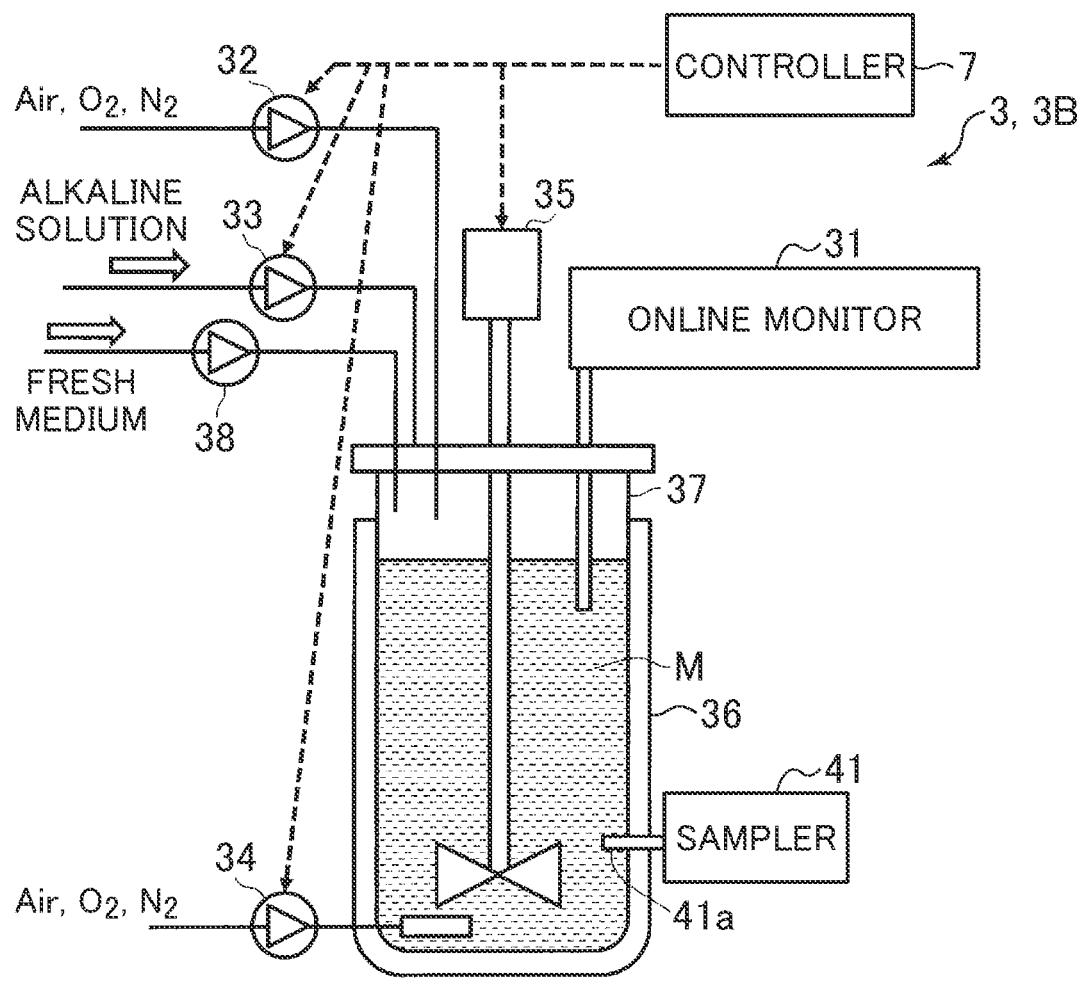
FIG. 7 is a schematic diagram of a culture apparatus according to a feeding culture system.

FIG. 7 schematically illustrates a culture apparatus for feeding culture. As illustrated in FIG. 7, the culture apparatus 3B for feeding culture, which is an example of the culturing device 3, has a configuration similar to that of the batch culture apparatus 3A, except for further including a medium feeder 38 that adds a fresh medium to the system. Likewise the batch culture apparatus 3A, the culture apparatus 3B for feeding culture measures the factors such as pH, DO, and temperature by the working of the online monitor 31, and controls, on the basis of the corresponding measured values, the devices 32 to 36 independently by the working of the controller 7 to allow the measured values to converge or approximate to predetermined controlling values. The medium feeder 38 feeds a fresh medium from an additional medium tank (not shown) to the culture M in the culture vessel 37 through peristaltic pumping or squeeze pumping, while controlling the flow rate and current velocity of the fresh medium. The flow rate and current velocity are set and regulated by the controller 7.

iii. Continuous Culture Apparatus

Figure 8:
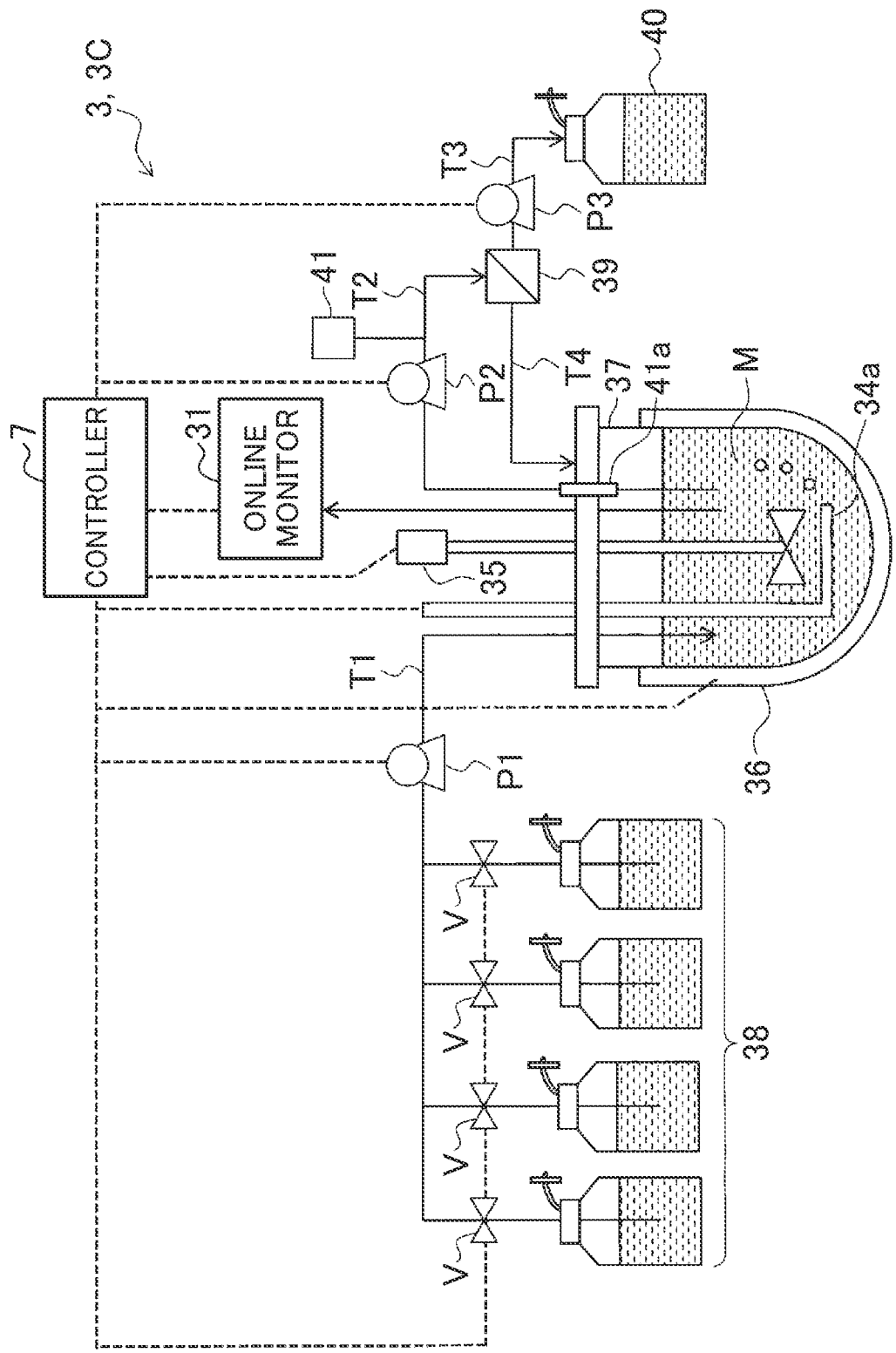
FIG. 8 is a schematic diagram of a culture apparatus according to a continuous culture system.

FIG. 8 schematically illustrate a continuous culture apparatus. As illustrated in FIG. 8, the continuous culture apparatus 3C, which is an example of the culturing device 3, typically includes a culture vessel 37, medium feeders 38, and a cell separator 39. The continuous culture apparatus 3C has a configuration similar to that of the culture apparatus 3B for feeding culture, except for further including the cell separator 39. The medium feeders 38 are coupled to the culture vessel 37 via valves V through a tube T1; the culture vessel 37 is coupled to the cell separator 39 through a tube T2; the cell separator 39 is coupled to a recovery vessel 40 through a tube T3; and the cell separator 39 is coupled to the culture vessel 37 through a tube 14. Of these tubes, the tubes T1, T2, and T3 are provided with pumps P1, P2, and P3 at optional positions.

The culture vessel 37 of the continuous culture apparatus 3C includes an agitator 35 that agitates the culture M, likewise the batch culture apparatus 3A and the culture apparatus 3B for feeding culture. The culture vessel 37 also includes a tubular air diffuser 34a for submerged bubbling, a temperature regulator 36, and an online monitor 31 that measures factors such as pH, DO, $DCO_2$, and temperature. The online monitor 31 includes sensors individually for measurement subjects. The culture vessel 37 also includes a tube (now shown in FIG. 8) for alkaline solution addition to control pH and DO to set values. The culture vessel 37 also includes a device (not shown in FIG. 8) for controlling alkaline addition and/or gas bubbling to maintain the culture environment within the predetermined set range on the basis of values obtained through the sensors. The controller 7 controls the monitored culture environmental factors independently for each device (unit) such as a gas phase oxygen concentration regulator (not shown in FIG. 8), a pH regulator (not shown in FIG. 8), a dissolved oxygen concentration regulator (not shown in FIG. 8), the agitator 35, or the temperature regulator 36. The control works on the basis of each measured value to allow the measured value to converge or approximate to a predetermined target value.

The continuous culture apparatus 3C as above, when used as the culturing device 3, can easily maintain the culture environment always constant and can stabilize the productivity.

The medium feeders 38 illustrated in FIG. 8 are each a device to add or feed a fresh liquid medium to the culture vessel 37 to compensate a nutritional component NC in the liquid medium, where the cell C has consumed the nutritional component NC in the culture vessel 37. The medium feeders 38 each have a tank (vessel) in which the fresh medium can be stored temporarily. The tank can be any vessel that can store the fresh medium temporarily. The fresh medium can be selected or prepared appropriately according to the cell C to be cultured.

The cell separator 39 illustrated in FIG. 8 is a device to separate the culture M in the culture vessel 37 into a cultured cell and a solution containing an antibody protein or another objective substance, and waste products. The cell separator 39 returns the cultured cell through the tube T4 to the culture vessel 37, and transfers the product (objective substance) and waste products through the tube T3 to the recovery vessel 40. Non-limiting examples of the separation technique of the cell separator 39 include gravitational settling, centrifugation, ultrasound aggregation, and separation by filtration. Any technique will do in the embodiment.

The recovery vessel 40 illustrated in FIG. 8 is a tank that temporarily stores the product and waste products separated by the working of the cell separator 39. The recovery vessel 40 can be any tank (vessel) capable of temporarily storing the product and waste products.

Culture Vessels 37

Figure 9:
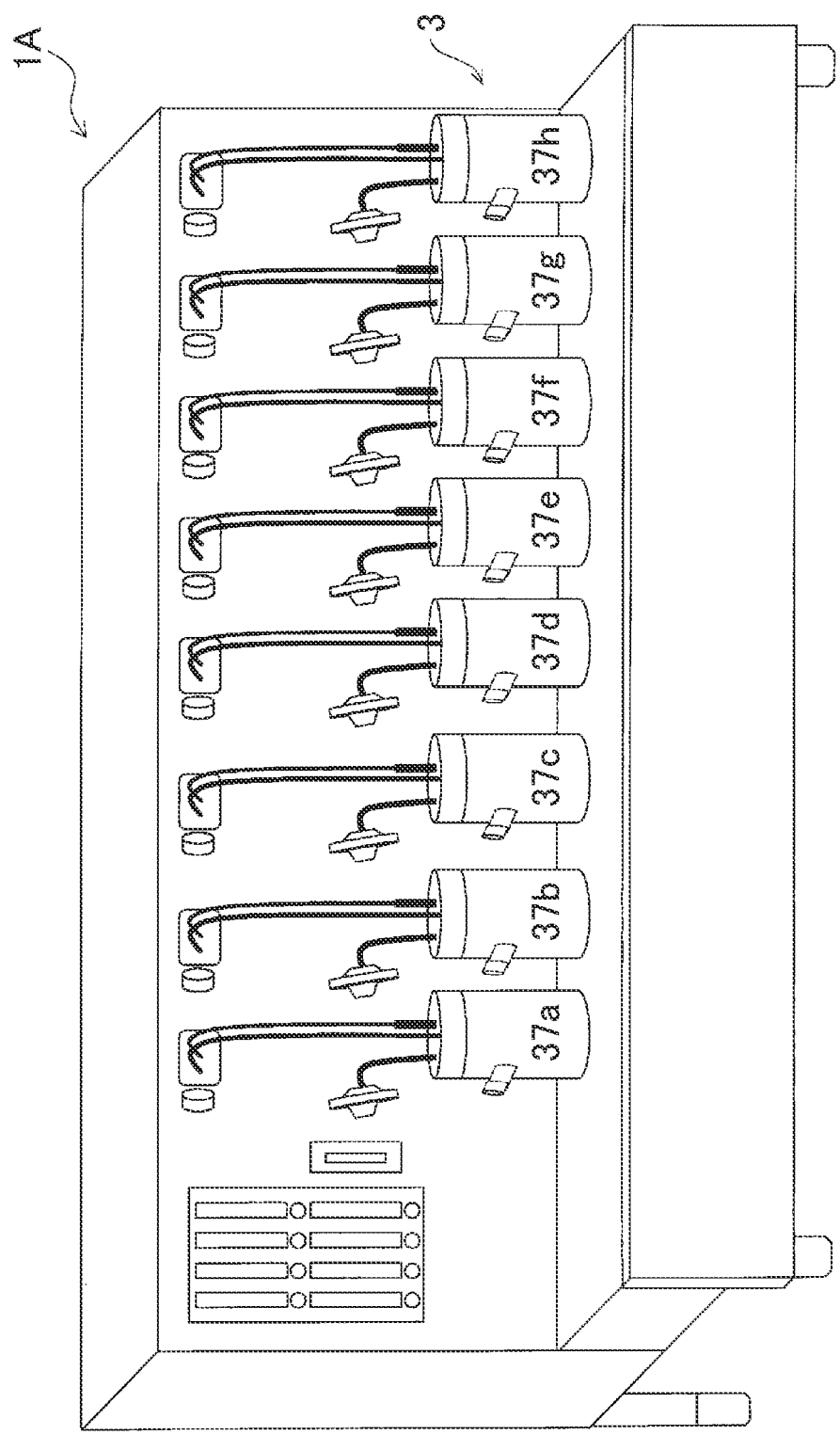
FIG. 9 is a schematic view of a screening apparatus equipped with culture vessels.

The culture apparatuses illustrated in FIGS. 6, 7, and 8 are those each including only one culture vessel 37. In general, gene-recombinant cells are stored as candidate cell lines (cell line pool). The screening apparatus 1 illustrated in FIG. 5 desirably includes multiple culture vessels 37 to make cultures under different culture conditions simultaneously. FIG. 9 schematically illustrates a screening apparatus including such culture vessels. The screening apparatus 1A illustrated in FIG. 9 includes culture vessels 37a to 37h typically having a capacity of 100 mL, as the culturing device 3. Though not shown in FIG. 9, the screening apparatus 1A includes medium feeders, cell separators, recovery vessels, and other devices individually coupled to the corresponding culture vessels 37a to 37h.

The culture vessels 37a to 37h in FIG. 9 each include a culturing device 3 having any of the configurations illustrated in FIGS. 6, 7, and 8. Accordingly, the culture vessels 37a to 37h can independently employ different culture control parameters such as number of revolutions in agitation, temperature, pH, DO, and $DCO_2$ and can measure and control these parameters. The culture vessels 37a to 37h can also independently measure and control other culture control parameters. Non-limiting examples of such other culture control parameters include the velocity of circulation from the culture vessels 37a to 37h via the corresponding cell separators, returning to the culture vessels 37a to 37h; the velocity of delivery from the cell separators to the corresponding recovery vessels; the adding rate to add a fresh media from the medium feeders to the corresponding culture vessels 37a to 37h; and the formulations of the fresh media.

The culture vessels 37a to 37h can employ these culture control parameters as screening subjects for culture conditions. A screening for a cell line having high productivity needs examination of a candidate cell line in combination with a culture condition suited for the cell line. Accordingly, the culture vessels 37 illustrated in FIGS. 6 to 8 are desirably configured to culture one candidate cell line in one system under different culture conditions. In contrast, the screening apparatus 1A illustrated in FIG. 9 can not only culture one cell line in one system in each of the eight culture vessels 37a to 37h, but also culture the one cell line in one system under different culture conditions by modifying or changing the controlling values of the culture conditions.

Analyzer 4

The analyzer 4 in FIG. 5 is a device to analyze a culture M containing the cells cultured in the culturing device 3. The analyzer 4 performs the analysis to give data (analysis results) necessary for metabolism analysis by the aftermentioned analysis value calculator 5. The analyzer 4 performs the analysis to verify whether the cells are in a stable state.

For the analysis, the analyzer 4 aseptically samples the culture M containing the cells cultured in the culturing device 3, as illustrated in FIG. 5. The aseptic sampling of the culture M can work with the sampler 41 illustrated in FIGS. 5 to 8. The sampler 41 can sample the culture M by sucking the culture M via a sampling port 41a provided in the culture vessel 37 as illustrated in FIGS. 6 to 8, using a pump P2 (see FIG. 8) such as a peristaltic pump. Assume that the culture vessel 37, the port 41a, the after-mentioned pretreater 42, and tubes coupling between them are made from pressure-tight glass, a stainless steel, or another material having pressure tightness and heat resistance. In this case, these devices and parts preferably receive vapor sterilization (at 121° C. for 20 minutes or longer) before and after sampling. When single-use devices such as single-use culture vessels and single-use tubes are used, it is acceptable that an aseptic connector, for example, is used as the port 41a, and a sampling tube is coupled to the port 41a on a sample by sample basis. The culture M can travel from the culture vessel 37 to the pretreater 42 using the pump P2 (see FIG. 8) such as a peristaltic pump, or through transfer under pressure.

The pretreater 42 in FIG. 5 is a device to perform a pretreatment suited for the analysis technique employed in the analyzer 4, before or upon the analysis of the components in the culture M or of the culture cell state by the analyzer 4. The pretreater 42 performs a pretreatment whose technique varies depending on the subject cell or the analysis technique. Examples of the pretreatment performed by the pretreater 42 are illustrated as flow charts in FIGS. 10A, 10B, 10C, and 10D.

Figure 10A:
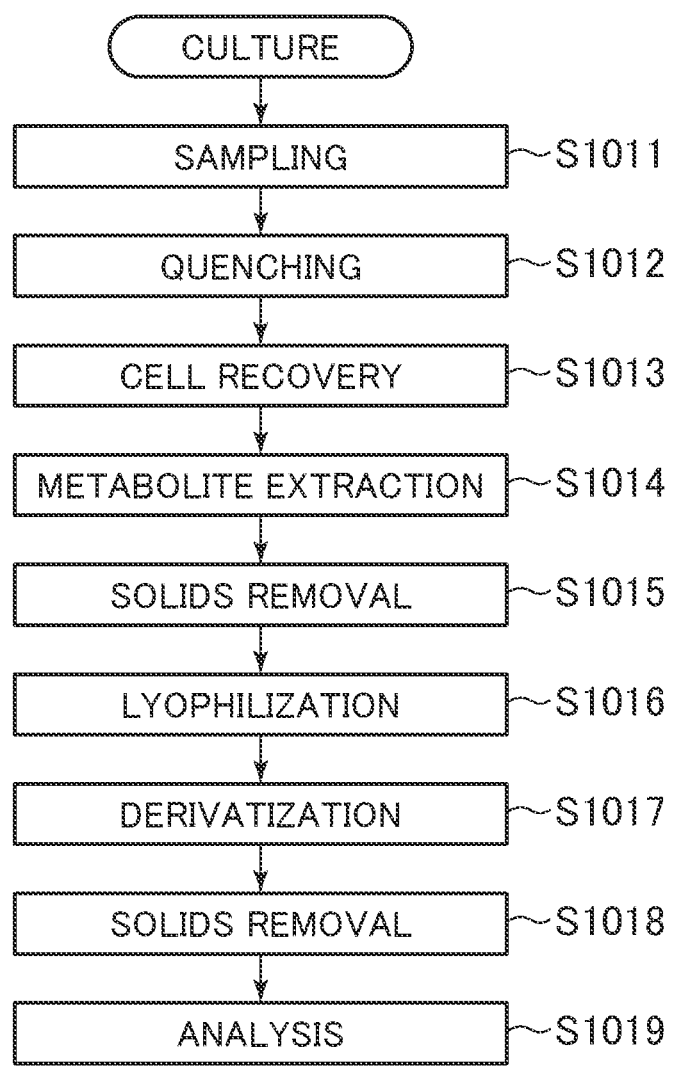
FIG. 10A is a flow chart illustrating exemplary pretreatments performed by a pretreater.

FIG. 10A illustrates one example of pretreatments performed between culturing to give a yeast cell extract and analysis. As illustrated in FIG. 10A, initially, a sample is taken from the culture M (Step S1011). The sample is taken typically in an amount corresponding to 5 mg of a dry biomass. The sample then receives quenching (Step S1012). The quenching works typically by injecting the sample into methanol at −50° C. (for example, 60% methanol in 10 mM 4-(2-hydroxyethyl)-1-piperazineethanesulfonic acid (HEPES), pH 7.5). Next, cells are recovered (Step S1013). The cells are recovered typically by centrifugation at −20° C., 10000×g for 5 minutes. Next, a metabolite is extracted (Step S1014). The metabolite is extracted typically by incubating the cells in 2 mL of boiling water (100° C.) for 15 minutes. Solids are then removed (Step S1015). The solids are removed typically by centrifugation at 10000×g for 5 minutes. Next, the sample receives lyophilization (freeze-drying) (Step S1016). The lyophilization works typically for 8 hours. Next, the sample receives derivatization (Step S1017). The derivatization works typically by bringing the sample into contact with 50 μL of N,N-dimethylformamide (DMF) (0.1% pyridine) and 50 μL of N-(tert-butyldimethylsilyl)-N-methyl-trifluoroacetamide (MBDSTFA) at 80° C. for 30 minutes. Next, solids are removed from the sample (Step S1018). The solids are removed typically by centrifugation at 10000×g for 5 minutes. Next, the sample is analyzed (Step S1019). The analysis works typically with a gas chromatograph-mass spectrometer, and can work by any technique according to the analysis subject.

Figure 10B:
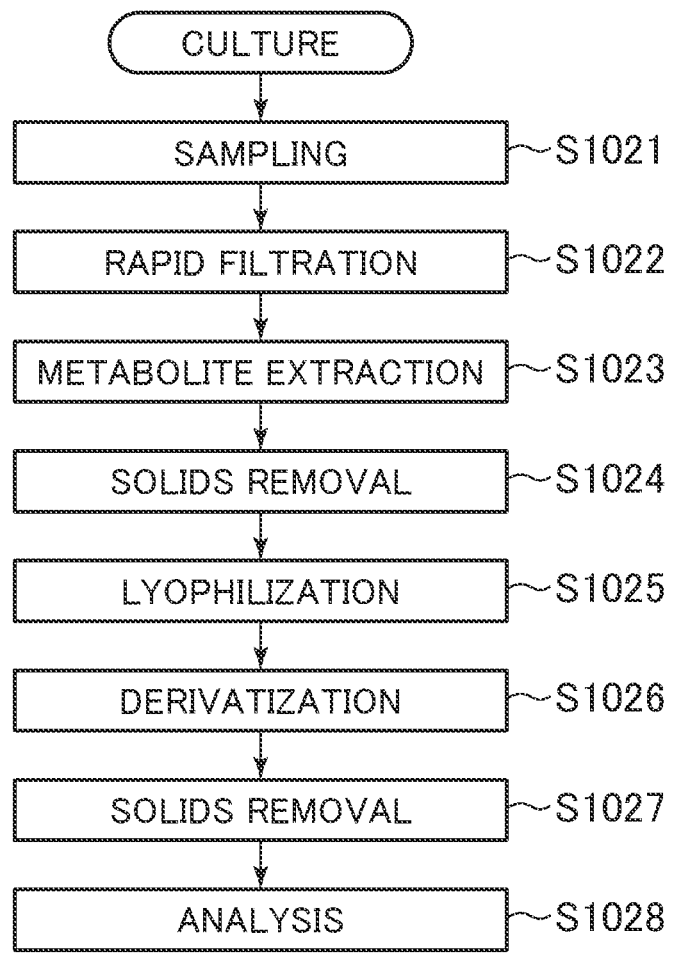
FIG. 10B is a flow chart illustrating exemplary pretreatments performed by a pretreater.

FIG. 10B illustrates one example of pretreatments performed between culturing to give a bacterial cell extract and analysis. As illustrated in FIG. 10B, initially, a sample is taken from the culture M (Step S1021). The sample is taken typically in an amount corresponding to 5 mg of a dry biomass. The sample then receives rapid filtration (Step S1022). The rapid filtration works typically by washing the sample two times with water through a nitrocellulose membrane filter (pore size: 0.2 μm). Then the sample sequentially receives metabolite extraction (Step S1023), solids removal (Step S1024), lyophilization (Step S1025), derivatization (Step S1026), solids removal (Step S1027), and analysis (Step S1028). The operations from the metabolite extraction (Step S1023) to the analysis (Step S1028) can work by procedures similar to those for the operations from the metabolite extraction (Step S1014) to the analysis (Step S1019) described above with reference to FIG. 10A.

Figure 10C:
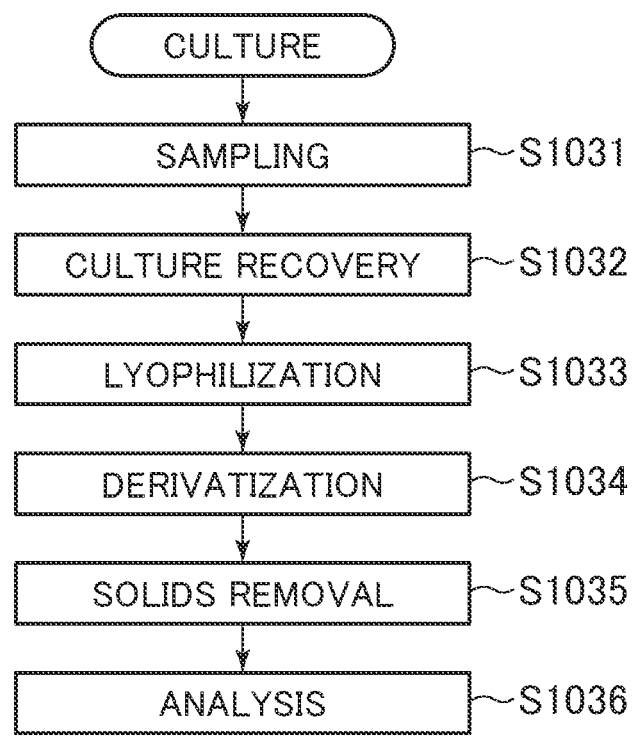
FIG. 10C is a flow chart illustrating exemplary pretreatments performed by a pretreater.

FIG. 10C illustrates one example of pretreatments performed between culturing to give a culture supernatant of the culture M and analysis. As illustrated in FIG. 10C, initially, a sample is taken from the culture M (Step S1031). The sample is sampled typically in an amount corresponding to 50 μL of the culture. Next, the culture M is recovered (Step S1032). The culture M is recovered typically by centrifugation at 10000×g for 5 minutes. The resulting sample sequentially receives lyophilization (Step S1033), derivatization (Step S1034), solids removal (Step S1035), and analysis (Step S1036). The operations from the lyophilization (Step S1033) to the analysis (Step S1036) can work by procedures similar to those for the operations from the lyophilization (Step S1016) to the analysis (Step S1019) described above with reference to FIG. 10A.

Figure 10D:
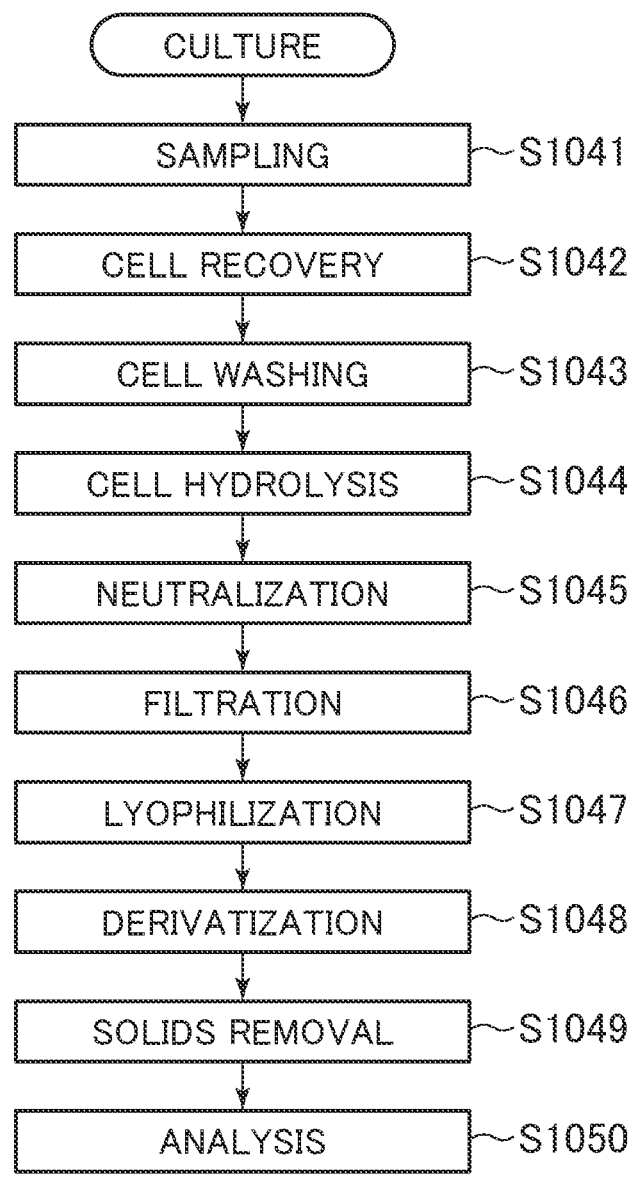
FIG. 10D is a flow chart illustrating exemplary pretreatments performed by a pretreater.

FIG. 10D illustrates one example of pretreatments performed between culturing to give a biomass (protein) hydrolysate and analysis. As illustrated in FIG. 10D, initially, a sample is taken from the culture M (Step S1041). The sample is sampled in an amount corresponding to 1 mg of a dry biomass. Next, cells are recovered (Step S1042). The cells are recovered typically by centrifugation at 10000×g for 5 minutes. Next, the cells are washed (Step S1043). The cells are washed typically with distilled water two times through centrifugation at 10000×g for 5 minutes. Next, the cells are hydrolyzed (Step S1044). The cells are hydrolyzed typically by treating the centrifuged precipitates (pellets) with 50 μL of 6 M HCl solution (hydrochloric acid) at 105° C. for 24 hours, where centrifuged precipitates and the 6 M HCl solution have been placed in a tube. Next, the hydrolysate receives a neutralization reaction (Step S1045). The neutralization reaction works typically using 6 M NaOH solution. The resulting sample undergoes filtration (Step S1046). The filtration works typically by centrifugation at 10000×g for 5 minutes using a centrifugal ultrafilter having a pore size of 0.2 μm. The sample then sequentially receives lyophilization (Step S1047), derivatization (Step S1048), solids removal (Step S1049), and analysis (Step S1050). The operations from the lyophilization (Step S1047) to the analysis (Step S1050) can work by procedures similar to those for the operations from the lyophilization (Step S1016) to the analysis (Step S1019) described above with reference to FIG. 10A.

Each pretreatment illustrated in FIGS. 10A, 10B, 10C, and 10D includes, as basic processes, reagent mixing, incubation with temperature control, centrifugation, and drying. Devices necessary herein include a mixer, a thermoregulator, a centrifuge, and a dryer. Each pretreatment works with a combination of processes using these devices. The processes can work manually, but preferably work automatically, in which robots, for example, automatically actuate devices for performing the steps and transportation of the sample between the devices. This configuration contributes to better authenticity of the pretreatments, and to reduction in working hours and labors.

Analysis by Analyzer 4

In the screening apparatus 1, the culture M is sampled from the culturing device 3, and is analyzed for cell state by the analyzer 4. The sampling works at an appropriate timing such as during a cell proliferative phase, or after the cells come into a product production phase subsequent to the cell proliferative phase, namely, after the cells reach a steady state. The analyzer 4 analyzes information that reflects the state of the analyzed cells by an appropriate technique and transmits the resulting analysis values to the analysis value calculator 5. Non-limiting examples of the information include product formation rate, nutrient substrate consumption rate, secretory rate of waste products and other by-products, cell proliferation rate, and intracellular metabolic reaction rate. Non-limiting examples of the analysis technique for the analysis subjects which can be analyzed by the analyzer 4 are as follows.

Analysis Subject I: Product Formation Rate

To determine the product formation rate, initially, a product in the culturing device 3 is analyzed for concentration. For example, the concentration of the target product, when being a protein, can be analyzed in the following manner.

The protein can be quantitatively analyzed using an enzyme-linked immunosorbent assay (ELISA). The ELISA uses an antibody that undergoes an antigen-antibody reaction with the measurement object protein, and calculates the concentration of the measurement object protein on the basis of the fluorescence or enzyme activity of the bound antibody. The determination through ELISA may work according to any technique such as direct technique, indirect technique, sandwich technique, or competition technique.

The product formation rate can be determined by measuring the time-dependent change of the protein concentration in the culture, and converting the change into the amount per unit time or per unit cell number.

Analysis Subject II: Nutrient Substrate Consumption Rate
Analysis Subject III: By-Products Secretory Rate To determine the nutrient substrate consumption rate and the by-products secretory rate (metabolite secretory rate), initially, the nutrient substrate concentration and the by-products concentration in the culturing device 3 are analyzed. As used herein, the term "nutrient substrate" refers to a medium component that is necessary for cell growth and/or product formation and is exemplified typically by inorganic ingredients, carbon sources, vitamins, and amino acids. Also as used herein, the term "by-products" refers to substances that are formed as by-products in a process of cell growth or product formation, and are exemplified typically by carbon dioxide gas, lactic acid, ammonia, pyruvic acid, and citric acid.

The nutrient substrate concentration and the by-products concentration are measured typically by measuring ingredients in the culture M from which the cells have been removed, using a device such as a high-performance liquid chromatograph (HPLC), liquid chromatograph-mass spectrometer (LC/MS), liquid chromatograph-tandem mass spectrometer (LC/MS-MS), gas chromatograph-mass spectrometer (GC/MS), or gas chromatograph-tandem mass spectrometer (GC/MS-MS). All of these analysis techniques (devices) can measure various different ingredients in the culture M at once.

The nutrient substrate consumption rate and the by-products secretory rate can be determined respectively by measuring the time-dependent changes of the nutrient substrate concentration and the by-products concentration, and converting the measurements into the amount of consumption and the amount of formation per unit time.

Analysis Subject IV: Cell Proliferation Rate

To determine the cell proliferation rate, initially, the number of cells in the culturing device 3 is analyzed. The number of cells can be measured by microscopic observation with a hemocytometer after trypan blue staining. The cell number can also be measured by another technique such as dry cell weight measurement, turbidimetry, static capacitor technique, nicotinamide adenine dinucleotide (NAD) measurement, or flow cytometry.

The cell proliferation rate µX is expressed by Formula 1:

$$\mu X = dX/dt \qquad \text{Formula 1}$$

wherein X represents the living cell number; µ represents the specific growth rate (cell proliferation rate); and t represents the time.

When the living cell numbers at two different points of time can be found, the specific growth rate can be determined using Formula 1. Assume that an error effect becomes non-negligible upon determination of the specific growth rate from the data at two different points of time. In this case, it is also accepted that the culture M, in which cells proliferate or grow exponentially, is sampled over time, and the specific growth rate is estimated on the basis of data in a larger number. For example, the data are plotted in a scatter plot with the abscissa indicating the culture time and the ordinate indicating the logarithmic value of the living cell number, and the slope of the plot (graph) is computed by the least square method. Assume that the graph is not obtained as a straight line. This indicates that the analyte cell does not exponentially grow, and there is some inhibitory factor during the culture period.

Analysis Subject V: Intracellular Metabolic Reaction Rate

The metabolic reaction rate is analyzed by analyzing an isotope ratio in an intracellular intermediate metabolite through the analysis of the sample, which has been treated by the pretreater 42, using a GC/MS, LC/MS, or nuclear magnetic resonance (NMR) system. To analyze the intracellular metabolic reaction rate and to perform the after-mentioned metabolism analysis, the cell is preferably cultured using an isotope-labeled substrate in a first culturing step S20 (see FIG. 12), as described later.

The intracellular metabolic reaction rate can be determined by measuring how the isotope ratio in an intracellular intermediate metabolite in the culture varies with time, and converting the data into the isotope ratio in the intermediate metabolite per unit time.

Analysis Subject VI: Cell Respiration Rate

The cell respiration rate can be analyzed by serial measurement of the oxygen consumption rate using a phosphorescent probe that quenches by the action of oxygen (such as MitoXpress).

The analysis results obtained in the above-mentioned analysis subjects I to VI are transmitted to the analysis value calculator 5 and used as input values.

Analysis Value Calculator 5

The analysis value calculator 5 shown in FIG. 5 is a device to perform a metabolism analysis on the basis of the analysis results from the analyzer 4, to determine analysis values by calculation. Namely, the analysis value calculator 5 is a device to compute or calculate a metabolic rate in the cell C. Techniques for the metabolism analysis are classified into one using an isotope-labeled substrate, and one using no isotope-labeled substrate. The metabolism analysis in the embodiment can employ any of these techniques. The metabolism analysis preferably employs the technique using an isotope-labeled substrate. This is because the technique can analyze: (1) the reaction rates of a forward reaction and a reverse reaction in a reversible reaction; (2) the reaction rate in a metabolic pathway including recycling; and (3) the reaction rate in a metabolic pathway which once branches, and the branched pathways then merge with each other. In addition, the technique can give higher precision in the metabolism analysis.

The technique using an isotope-labeled substrate for use herein can advantageously be $^{13}$C-metabolic flux analysis ($^{13}$C-MFA). The $^{13}$C-MFA is a technique which utilizes the fact that the isotopic distribution varies when fed $^{13}$C-labeled carbon atoms are metabolized in the cell or pass through different pathways in a metabolic pathway network. The technique can determine the metabolic reaction rate from the isotope balance.

The technique using no isotope-labeled substrate for use herein can advantageously be a metabolic reaction rate analysis (flux balance analysis; FBA) on the basis of a stoichiometric equation. The FBA can determine an unmeasurable metabolic reaction rate by measuring how the concentration of a metabolite in the cell varies with time during culture, and determining the unmeasurable metabolic reaction rate on the basis of the formation rate of the metabolite and the material balance.

As an example of the analysis value calculator 5, a method for analyzing a metabolic flux by metabolism analysis using an isotope-labeled substrate will be illustrated below.

Figure 11:
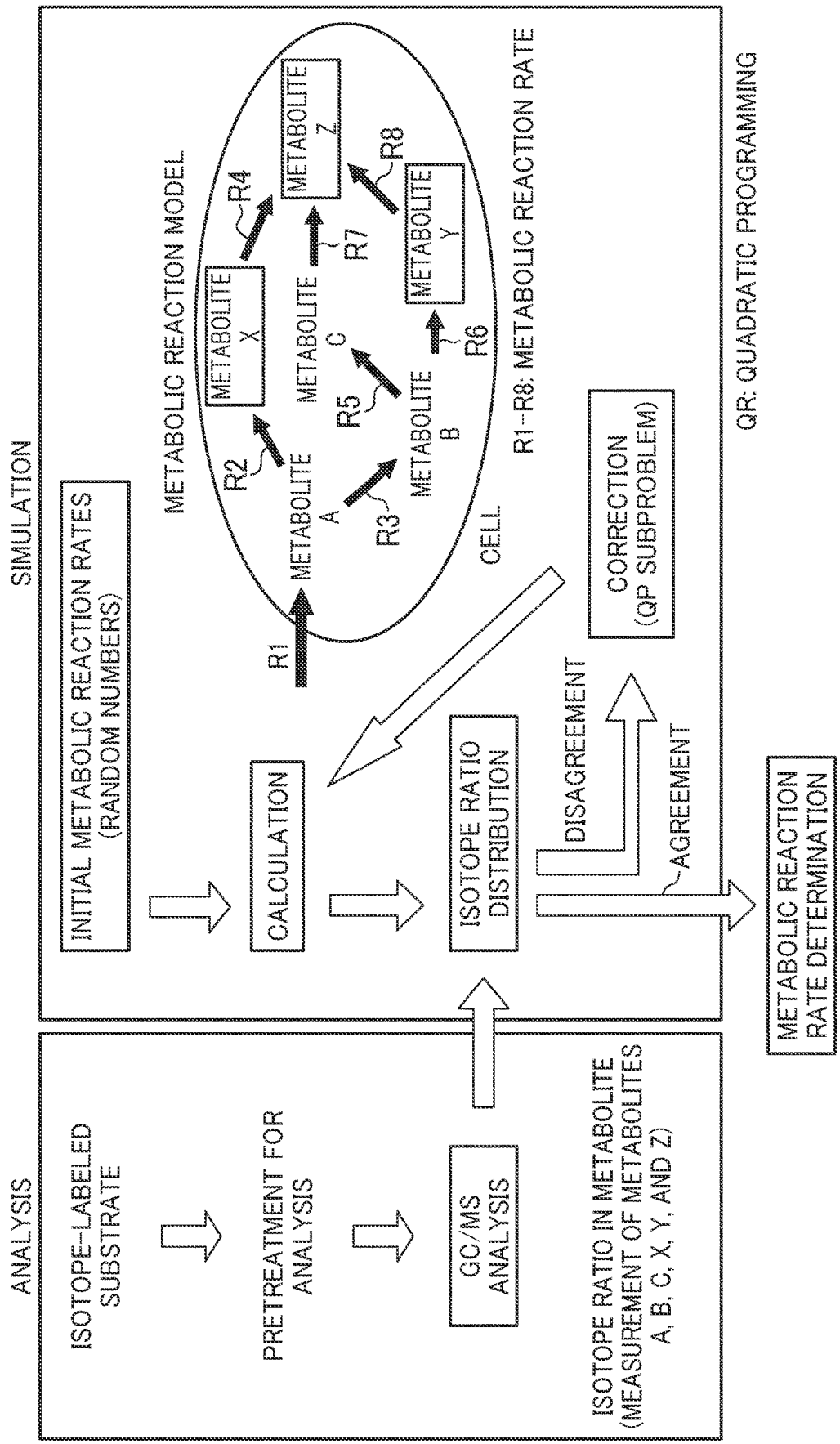
FIG. 11 explanatorily conceptually illustrates a metabolic flux analysis method.

FIG. 11 explanatorily illustrates the concept of the method for analyzing a metabolic flux.

In a simulation illustrated in FIG. 11, random metabolic flux values (initial metabolic reaction rates (random numbers)) are given at the start (as R1 to R8 in FIG. 11). On the basis of a metabolic pathway model, the ratios of numbers of carbon isotopes contained in metabolites A, B, C, X, Y, and Z in the cell C in a steady state are calculated. The calculated values are compared with the carbon isotope number ratios of the metabolites A, B, C, X, Y, and Z in the cell, which ratios have been analyzed (actually measured) by the analyzer 4. When the two isotope ratio distributions are not statistically significantly different from each other (when the two approximately agree with each other), the simulated metabolic reaction rates (metabolic fluxes) are determined as estimated metabolic fluxes. In contrast, when the two isotope ratio distributions are statistically significantly different from each other (when the two disagree with each other), the simulated metabolic flux values are corrected to minimize the mean square error between the simulated carbon isotope number ratios in the metabolites and the experimental carbon isotope number ratios in the metabolites. The correction can work typically using a quadratic programming (QP) subproblem. Using the QP subproblem, the correction works in the following manner. Assume that the carbon isotope number ratios in the formed specific metabolites A, B, C, X, Y, and Z statistically significantly differ from the simulated carbon isotope number ratios in the specific metabolites A, B, C, X, Y, and Z. In this case, to allow a mean square error between the two to fall within the preset predetermined range and to be minimized, among the simulated respective metabolic fluxes in the metabolic pathways R1 to R8, a metabolic flux that relates to the error in the metabolic pathways R1 to R8 is corrected. As is described above, when the simulated results disagree with the experimental results, one repeats the operation of computing a carbon isotope ratio on the basis of a corrected metabolic flux, and comparing the computed (simulated) carbon isotope ratio with the experimental carbon isotope number ratio in the metabolites until there is no statistically significant difference in the isotope ratio distribution. When the simulated results agree with the experimental results, the metabolic reaction rates (metabolic fluxes) are determined on the basis of the simulated results.

The analysis value calculator 5 performs the metabolism analysis to determine analysis values by calculation, preferably after the culture cells reach a steady state. This allows a stable metabolism analysis. Whether the cells are in a steady state is determined preferably according to at least one index selected from the nutrient substrate consumption rate in the culture cells, the by-products secretory rate in the culture cells, and the cell respiration rate in the culture cells, each alone or in combination. This configuration allows easy and reliable determination whether the culture cells are in a steady state. Preferably, the analysis value calculator 5 determines whether the culture cells are in a steady state on the basis of the analysis results from the analyzer 4. As illustrated in FIG. 5, the analysis value calculator 5 preferably includes a determiner 51 to perform such determination. The determiner 51 checks that the culture cells are in a steady state, preferably before the analysis value calculator 5 calculates the analysis values. This configuration can avoid a metabolism analysis on culture cells that are not in a steady state, and contributes to labor savings. The determination of the steady state will be described later.

Metabolic Database DB

The metabolic database DB illustrated in FIG. 5 is a device to correct correlations between the culture environmental factors such as DO, Tem, and pH and the corresponding metabolic rate formulae. The metabolic database DB gives a stored correlation model to the after-mentioned culture condition computer 61 when the culture condition computer 61 computes an optimal culture condition. Examples of the metabolic reactions and examples of the correlation models will be illustrated below, with reference to FIG. 11. In the examples of the metabolic reactions and the examples of the correlation models, A, B, C, and Z represent metabolites; f represents the reaction rate; pH, DO, and Tem represent the culture environmental factors, where DO represents the dissolved oxygen concentration, and Tem represents the temperature.

Examples of Metabolic Reactions

Metabolic reaction number R3: A→B,
Metabolic reaction number R5: B→C,
Metabolic reaction number R7: C→Z,
. . .

Examples of Correlation Models

Metabolic rate formula R3: $f_{A \to B} \propto$ pH, DO,
Metabolic rate formula R5: $f_{B \to C} \propto$ Tem,
Metabolic rate formula R7: $f_{C \to Z} \propto$ DO, Tem,
. . .

As is described above, the correlation models are preferably defined using metabolic rate formulae having culture conditions as parameters. This contributes to higher conformity between the parameters used in computation of culture conditions by the culture condition computer 61 and the culture conditions resulting from the computation.

Examples of the metabolic reaction formulae include the metabolic reaction formulae mentioned above in the "Reaction Numbers and Metabolic Reaction Formulae in FIG. 4". The reaction rates in the metabolic reaction formulae can each be determined by the method described above in "Analysis Subject V: Intracellular Metabolic Reaction Rate". Non-limiting examples of the culture environmental factors include DO, $DCO_2$, pH, temperature (Tem), shear stress, nutrient substrate concentration, metabolite concentration, and osmotic pressure. The metabolic reaction rates and culture environmental factors are not limited to those mentioned above.

The correlation model stored in the metabolic database DB can be repeatedly corrected by making a database of new information in a manner as described in the examples of metabolic reactions and the correlation model, where the new information is obtained typically when papers or articles, journals, books, experiment data, or any other information is released or published; or when culture results (such as the analysis values) are obtained in screening. The repeated correction of the correlation model can operate before the calculation by the culture condition computer 61 operates. The repeated correction of the correlation model can work typically with a correlation model corrector 60 of the culture condition simulator 6 illustrated in FIG. 5. The correlation model corrector 60 works as one of functions of the culture condition simulator 6. The correlation model corrector 60 compares the analysis values with the correlation model stored in the metabolic database DB, and performs a correction computation as needed to correct the correlation model as described above. Non-limiting examples of the analysis values include the metabolic reaction formulae R3, R5, R7 . . . in the "Examples of Correlation Model". The correlation model correction preferably works typically when the correlation model stored in the metabolic database DB differs, by greater than ±10%, from the culture results (specifically, a correlation model calculated from the culture results).

Culture Condition Computer 61

The culture condition computer 61 illustrated in FIG. 5 is a device to compute a culture condition (optimal culture condition) which gives an analysis value, among the analysis values, most close to the target value, where the computation works with the correlation model which is preset, or corrected by the correlation model corrector 60. Then the culture condition computer 61 modifies the culture condition set in the culturing device 3 to the computed culture condition (optimal culture condition). The culture condition computer 61 works as one of functions of the culture condition simulator 6. The culture condition computer 61 applies a specific culture condition, namely, specific culture environmental factors, to the correlation model and sets an intracellular metabolic reaction model, to approximate the correlation model to the target values relating to the metabolic reactions of the culture cell, which target values are set by the working of the target value setter 2. The culture condition computer 61 computes a culture condition under which values obtained according to the intracellular metabolic reaction model be most close to the target values. The specific culture conditions are each a constant value or a varying value which is set on the culture environmental factor and can be determined on the basis of the data stored in the metabolic database DB. A non-limiting example of the calculated values calculated in the above manner is an integrated value of values calculated according to the metabolic reaction formulae of the correlation model. The modified culture condition is sent to the culturing device 3, to which the set culture condition is modified. Once the culture condition is modified, the culturing device 3 performs a next cell culture under the modified culture condition.

Screener 62

The screener 62 in FIG. 5 is a device for the screening of the analysis values resulting from analyses on different culture cells and different culture conditions, for a cell line and a culture condition each of which gives a value most close to the target value. The screener 62 works as one of functions of the culture condition simulator 6. The screener 62 typically includes a selection device 63 and a screening device 64.

The selection device 63 is a device or mechanism that selects an optimal culture condition on the basis of the analysis values resulting from cultures performed on different culture cells and different culture conditions.

The screening device 64 is a device or mechanism that evaluates metabolic reaction rates and amount of an objective substance in cells cultured under the optimal culture condition, for the screening for a cell line to be used in cell culture.

The screener 62 allows a screening of the analysis values resulting from analyses on different culture cells and different culture conditions, for a cell line and a culture condition each of which gives values most close to the target values, as described above. This is done through the selection of an optimal culture condition by the selection device 63 and the screening for a cell line by the screening device 64.

Controller 7

The controller 7 in FIG. 5 is a general-purpose computer, a personal computer, or another device including a CPU and a storage medium such as a hard disk drive. The controller 7 functions as a predetermined device by storing a predetermined program in the storage medium, and reading out the stored program.

The controller 7 receives parameter values of the culture condition (optimal culture condition) sent from the culture condition computer 61 and controls the operation of the culturing device 3. For example, to raise the temperature, the controller applies heat to the temperature regulator 36 of the culturing device 3; and, to lower the temperature, the controller drives a water-cooling device. Thus, the controller adjusts the temperature to the target temperature. To increase the pH, the controller charges an alkaline solution into the culturing device 3; and, to lower the pH, the controller charges an acidic solution into the culturing device 3. To increase the dissolved oxygen concentration, the controller bubbles air or pure oxygen into the culture M in the culturing device 3; and, to lower the dissolved oxygen concentration, the controller bubbles nitrogen into the culture M in the culturing device 3. To increase the shear stress, the controller increases the number of revolutions of agitating elements of the agitator 35; and, to lower the shear stress, the controller decreases the number of revolutions of agitating elements of the agitator 35. Other parameters are also controlled by techniques suitable for the control of the parameters.

Embodiment of Screening Method

Next, an embodiment of the screening method will be illustrated. In the following description, an element which is the same with one in the screening apparatus 1 is indicated with the same referential sign, and detailed description thereof will be omitted.

Figure 12:
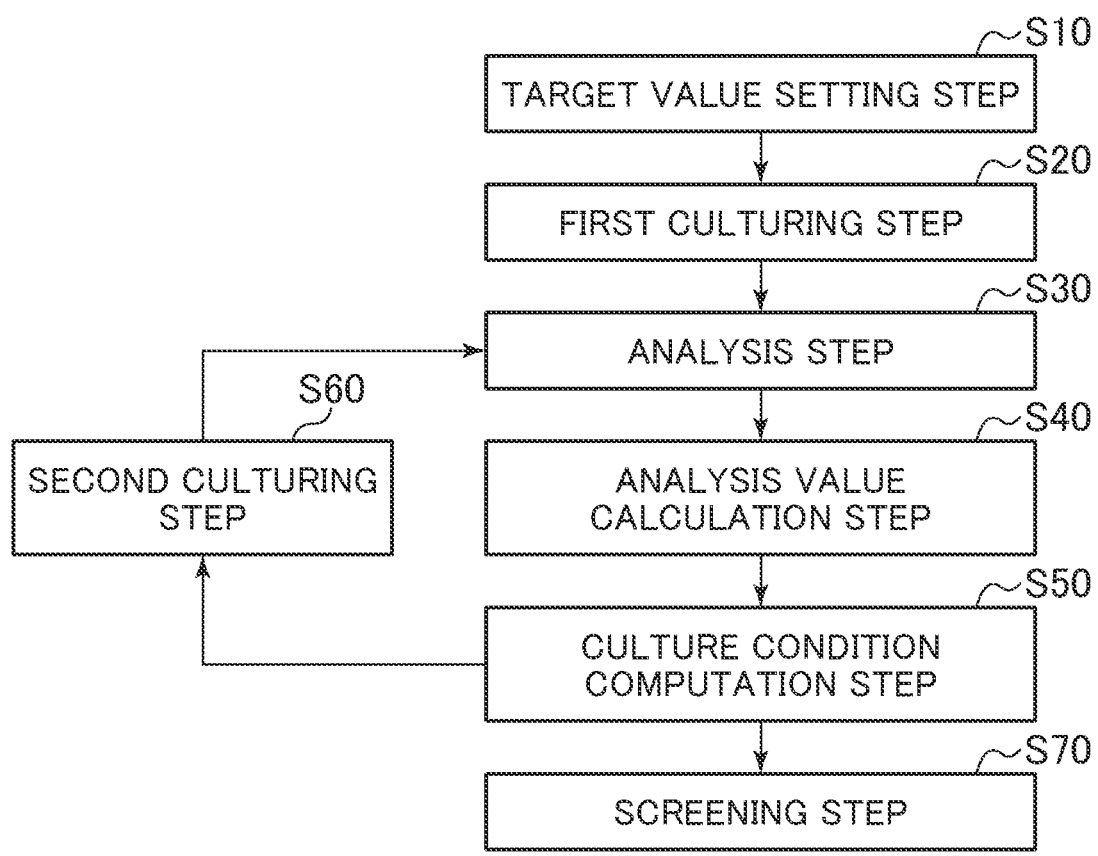
FIG. 12 is a flow chart illustrating steps included in a method according to the embodiment for screening of cell lines and culture conditions.

FIG. 12 is a flow chart illustrating the details of the screening method according to the embodiment.

As illustrated in FIG. 12, the screening method includes a target value setting step S10, a first culturing step S20, an analysis step S30, an analysis value calculation step S40, a culture condition computation step S50, a second culturing step S60, and a screening step S70.

The target value setting step S10 is the step of setting a target value relating to a metabolic reaction in a culture cell. The target value setting step S10 can work with the target value setter 2.

The first culturing step S20 is the step of culturing the culture cell under a preset culture condition. The first culturing step S20 can work with the culturing device 3.

The analysis step S30 is the step of analyzing a culture (culture solution) including the cultured cell resulting from culturing in the first culturing step S10. The analysis in the analysis step S30 works to give an analysis value relating to an index such as product formation rate, product concentration, or medium components, to determine whether the cultured cell is in a steady state. The analysis step S30 can work with the analyzer 4.

The analysis value calculation step S40 is the step of performing a metabolism analysis on the basis of analysis results from the analysis step S30, to determine analysis values by calculation. The analysis value calculation step S40 can work with the analysis value calculator 5. The method according to the embodiment may include a determination step S41 (not shown in FIG. 12, see FIG. 13) upstream from the analysis value calculation step S40. The determination step S41 is the step of determining whether the cultured cell is in a steady state on the basis of the analysis results from the analysis step S30. The analysis value calculation step S40 performs the metabolism analysis preferably after the culture cell reaches a steady state. This can avoid or minimize a metabolism analysis on a cultured cell not in a steady state. The determination step S41 can work with the determiner 51 in FIG. 5.

The analysis value calculation step S40 (specifically, the determination step S41) determines whether the cultured cell is in a steady state preferably using at least one index selected from the culture cell nutrient substrate consumption rate, the culture cell by-products secretory rate, and the culture cell respiration rate, alone or in combination. This allows easy and precise determination whether the cultured cell is in a steady state.

The culture condition computation step S50 is the step of computing, using a correlation model, a culture condition that gives an analysis value, among the analysis values, most close to the target value, and modifying the culture condition set in the first culturing step S20 to the computed culture condition. The culture condition computation step S50 can work with the culture condition computer 61. The screening method according to the embodiment may further include a correlation model correction step S51 (not shown in FIG. 12, see FIG. 13) as an upstream step from the culture condition computation step S50. The correlation model correction step S51 is the step of correcting a correlation model stored in the metabolic database DB on the basis typically of a culture result in screening, such as the analysis values from the analysis value calculation step S40. The correlation model correction step S51 can work with the correlation model corrector 60 shown in FIG. 5.

The second culturing step S60 is the step of culturing a cell belonging to the same culture line with the above-mentioned culture cell, under the modified culture condition modified in the culture condition computation step S50, and sending the resulting culture M to the analysis step S30. The second culturing step S60 can work with the culturing device 3, as with the first culturing step S20. Specifically, the first culturing step S20 and the second culturing step S60 differ from each other only in that a culture cell is cultured under the preset culture condition, or a culture cell is cultured under the culture condition modified in the culture condition computation step S50; and the two steps are approximately the same in details of the step.

The screening method according to the embodiment performs a series of the steps from the analysis step S30 to the second culturing step S60 on different culture cells and different culture conditions.

The screening step S70 is the step for the screening for a cell line and a culture condition each of which gives an analysis value, among the resulting analysis values, most close to the target value. The screening step S70 can work with the screener 62.

More Detailed Form of Screening Method

A more detailed form of the screening method will be illustrated below.

Figure 13:
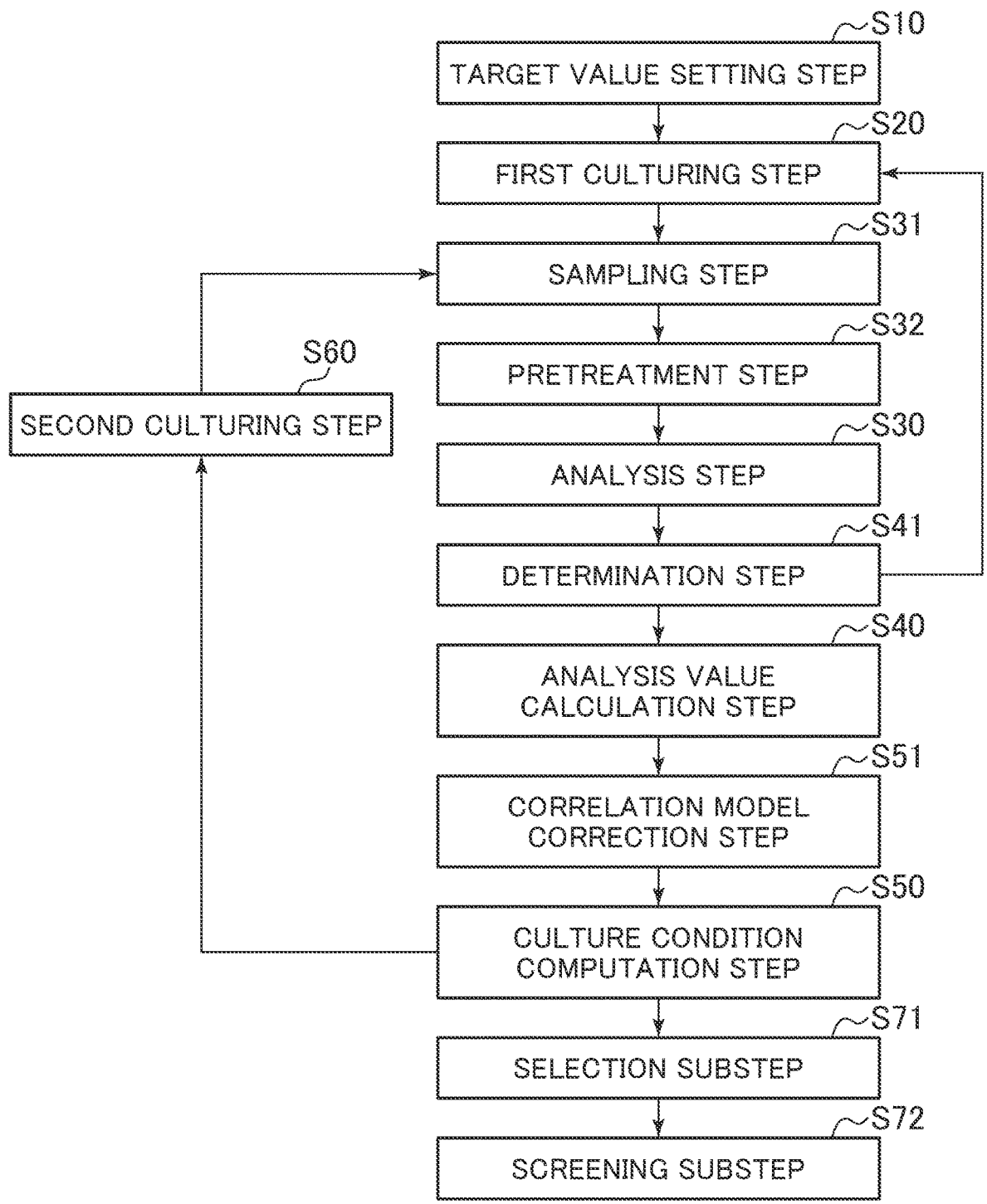
FIG. 13 is a flow chart illustrating steps included in a further detailed form of the method according to the embodiment for screening of cell lines and culture conditions.

FIG. 13 is a flow chart illustrating details of a more detailed form of the screening method according to the embodiment.

As illustrated in FIG. 13, the screening method includes a target value setting step S10, a first culturing step S20, a sampling step S31, a pretreatment step S32, an analysis step S30, a determination step S41, an analysis value calculation step S40, a correlation model correction step S51, a culture condition computation step S50, a second culturing step S60, a selection substep S71, and a screening substep S72. The method according to the form performs a series of the steps from the sampling step S31 to the second culturing step S60 on different culture cells and different culture conditions.

Of these steps, the target value setting step S10, the first culturing step S20, the analysis step S30, the analysis value calculation step S40, the culture condition computation step S50, and the second culturing step S60 are as with those mentioned above and are referred to the above description, the detailed description of which will not be omitted herein.

The sampling step S31 is the step of aseptically sampling a culture (culture solution) M. The sampling step S31 works with the sampler 41.

The pretreatment step S32 is the step of performing one or more pretreatments necessary for the analysis of the sampled culture M. The pretreatment step S32 works with the pretreater 42.

The determination step S41 is the step of determining whether the cultured cell is in a steady state, on the basis of the analysis values from the analysis step S30. When the cultured cell is found to be not in a steady state as a result of determination in the determination step S41, the culturing continues without modification (return to the first culturing step S20). When the cultured cell is found to be in a steady state as a result of determination in the determination step S41, go to the analysis value calculation step S40. The determination step S41 works with the determiner 51 of the analysis value calculator 5 (see FIG. 5).

The correlation model correction step S51 is the step of correcting the correlation model on the basis of the culture result obtained in screening. Specifically, the correlation model correction step S51 is the step of correcting the correlation model stored in the metabolic database DB, typically on the basis of the analysis values from the analysis value calculation step S40. The correlation model correction step S51 works with the correlation model corrector 60 of the culture condition simulator 6 (see FIG. 5), as described above. The correlation model correction step S51 can repeatedly correct the correlation model until the screening method completes, on each screening under a modified (different) culture condition, namely, on each performing of a series of the steps including the second culturing step S60, the analysis step S30, the analysis value calculation step S40, and the culture condition computation step S50.

The selection substep S71 and the screening substep S72 are substeps performed in the screening step S70.

The selection substep S71 is the step of selecting an optimal culture condition on the basis of the analysis values obtained by culturing different culture cells under different culture conditions. The selection substep S71 selects the optimal culture condition preferably on the basis typically of at least one analytical data selected from the cell proliferation rate, cell cycle, and metabolic flux. The selection substep S71 works with the selection device 63.

The screening substep S72 is the step of evaluating factors such as the metabolic reaction rate and the amount of the formed objective substance in the cell cultured under the optimal culture condition, and whereby screening for a cell line for cell culture. The screening substep S72 works with the screening device 64.

Still More Detailed Form of Screening Method

Figure 14:
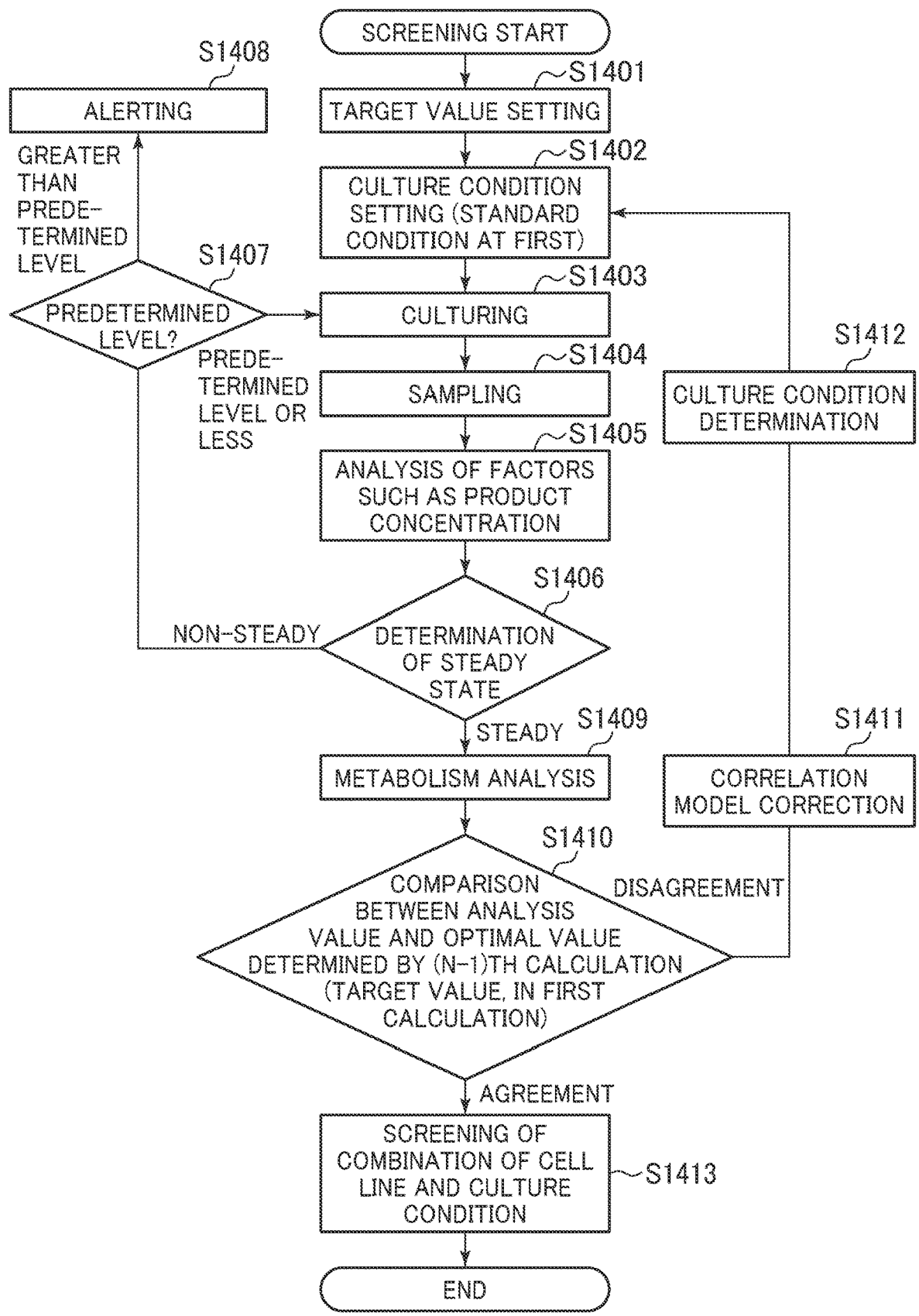
FIG. 14 is a flow chart illustrating steps included in a further detailed form of the method according to the embodiment for screening of cell lines and culture conditions.

Next, a still more detained form of the screening method will be illustrated below, with reference to FIG. 14. FIG. 14 is a flow chart illustrating details of a still more detailed form of the screening method according to the embodiment.

As illustrated in FIG. 14, the screening method initially sets a metabolic pathway model and a target metabolic reaction rate (step S1401). The step S1401 works with the target value setting step S10.

Next, the method sets an initial culture condition in the culturing device 3 (culture condition setting, step S1402), and starts culturing (step S1403). The culturing preferably employs an isotope-labeled substrate. This allows the aftermentioned metabolism analysis to work more precisely.

The initial culture condition can be set as a preset standard condition and can be set optionally. The culture cell immediately after the culture start is in a non-steady state and is sampled at predetermined time intervals (step S1404). The steps S1402 and S1403 work in the first culturing step S20, and the step S1404 works in the analysis step S30 (specifically, in the sampling step S31).

Then factors such as a product concentration and medium components are analyzed (step S1405). Specifically, factors to be analyzed are, in addition to the product concentration and the medium components, one or more factors that reflect the state of the cell, such as a product formation rate, a nutrient substrate consumption rate, and a by-products secretory rate. The step S1405 works in the analysis step S30, where necessary after the pretreatment step S32.

The culture cell is determined to be in a steady state when the analysis values in the step S1405 become constant without change with time (determined as "steady" in the step S1406). In contrast, as compared with the data from the previous sampling, when any of the values of factors changes with time, the culture cell is determined not to reach a steady state (determined as "non-steady" in the step S1406), where non-limiting examples of the factors include product concentration, medium components, product formation rate, nutrient substrate consumption rate, by-products secretory rate, and intracellular metabolic flux. The step S1407 then analyzes a non-steady period. When the period exceeds a predetermined level, for example, when the cell does not reach a steady state after a set number of samplings or after a set culture time is elapsed, an alert is displayed (step S1408). The non-steady period is analyzed, and, when the period is at a predetermined level or shorter, return to the step S1403 to continue the culture.

The step S1405 works in the analysis step S30 (and the pretreatment step S32), and the step S1406 works in the determination step S41.

When the culture cell is in a steady state (when determined as "steady" in the step S1406), factors such as the product formation rate, cell proliferation rate, and metabolic flux receive a metabolism analysis to give analysis values (step S1409). The step S1409 preferably performs a simulation typically by QP subproblem according to necessity, as described above, to determine the metabolic reaction rates (metabolic fluxes).

The analysis values (such as analysis values of metabolic reaction rates) resulting from the metabolism analysis are recorded, and the analysis values are compared with corresponding optimal values (such as optimal values of metabolic reaction rates) under the optimal culture condition resulting from a previous ((N−1)th) computation (step S1410). When the comparison is a first comparison, the optimal values can be replaced with target values (such as target metabolic reaction rates) set in the step S1401.

When an analysis value resulting from the metabolism analysis disagrees with an optimal value resulting from the (N−1)th computation ("disagreement" in the step S1410), the correlation model typically between the culture environmental factor and the metabolic reaction rate is corrected to give a metabolic reaction rate that agrees with the metabolic reaction rate resulting from the analysis of the culture experiment (step S1411).

Using the corrected correlation model, a culture condition that gives a value most close to the target value is determined (step S1412), where the target value is set in the step S1401. After returning to the step S1402, the previously set culture condition is changed to the determined culture condition (step S1402), and a culturing starts under the newly set condition in the culturing device 3 (step S1403).

In contrast, when the analysis value resulting from the metabolism analysis agrees with the optimal value resulting from the (N−1)th computation ("agreement" in the step S1410), the correlation model between the culture environmental factor and the metabolic reaction rate is evaluated as having high precision, and the culture condition in this culturing is optimized to approach the set target value.

When there is another candidate cell line, a culturing and subsequent treatments work on the other candidate cell line to give an analysis value, and this analysis value is further compared with the optimal value. After repeating this process, finally, a cell line and a culture condition each of which gives an analysis value most close to the target value (has highest productivity) are selected and screened (step S1413). Thus, the screening completes.

The steps S1409 and S1410 work in the culture condition computation step S50. The steps S1411 and S1412 work in the correlation model correction step S51. The culturing (step S1403) after the step S1412 and the step S1402 works in the second culturing step S60. The step S1413 works in the screening step S70 (specifically, in the selection substep S71 and the screening substep S72).

Modification

The procedure has been illustrated as an example (embodiment). In a modification, for example, the metabolism analysis (the step S1409) may employ an analysis for estimating a metabolic flux on the basis of a metabolite in the culture M, instead of the metabolism analysis using an isotope-labeled substrate. In another modification, the metabolism analysis may employ an analysis for estimating a metabolic flux on the basis of mRNA measurement. These configurations eliminate the need for isotopes, are easy and simple typically in operation and disposal of the culture, and can work inexpensively.

In FIG. 5, the analysis value calculator 5, the culture condition simulator 6, and the controller 7 are illustrated as independent devices. However, these can be one device (computer) that stores a program to actualize these means or functions.

The method and apparatus according to the embodiment for screening of cell lines and culture conditions as described above allow easy screening for a cell line and a culture condition each of which gives a value close to a target value (such as a metabolic reaction rate). The method and apparatus also allow, in the process of screening, formularization (modeling) of a relationship between a culture environmental factor and a target value typically of a metabolic reaction rate. The method and apparatus according to the embodiment for screening of cell lines and culture conditions can find a most efficient metabolic reaction pathway with a few number of culture conditions and allow inexpensive screening. The method and apparatus according to the embodiment for screening of cell lines and culture conditions construct a model relating to comprehensive metabolic pathways and can efficiently suppress production of unnecessary substances such as by-products. Thus, the use of a cell line found as a result of screening by the method and apparatus can give an objective substance with less variation in quality and with high productivity.

The method and apparatus according to the present invention for screening of cell lines and culture conditions have been described above in detail with reference to several embodiments or forms thereof. It should be noted, however, that the embodiments and forms are by no means intended to limit the scope of the invention; and that various changes and modifications should be considered to be within the scope of the invention. For example, the embodiments and forms are described in detail for illustrative purpose only, and the present invention is not limited to ones having all the illustrated configurations. It is possible that a portion of a configuration of an embodiment is replaced with a configuration of another embodiment; that a configuration of an embodiment is combined with a configuration of another embodiment; and that a portion of a configuration of each embodiment is combined with or replaced with a configuration of another embodiment, or is deleted.

LIST OF REFERENCE SIGNS

S10 target value setting step
S20 first culturing step
S30 analysis step
S40 analysis value calculation step
S50 culture condition computation step
S60 second culturing step
S70 screening step
1, 1A screening apparatus
2 target value setter
3 culturing device
4 analyzer
5 analysis value calculator
6 culture condition simulator
61 culture condition computer
62 screener
7 controller
DB metabolic database

The invention claimed is:

1. A method for screening of cell lines and culture conditions, the method comprising:
a target value setting step of setting a target value for a metabolic reaction of a culture cell;
a first culturing step of culturing a plurality of culture cells under a preset culture conditions;
a sampling step for obtaining a culture solution including a cultured cell from the first
culturing step:
an analysis step of analyzing the culture solution including the cultured cell to provide an analysis result;
an analysis value calculation step of determining whether the cultured cell is in a steady state based on the analysis result and performing a metabolism analysis to determine a metabolic reaction rate based on the analysis result from the
analysis step, and determining an analysis value by calculation;
a correlation model correction step of correcting a correlation model using the analysis value;
a culture condition computation step of computing, using the corrected correlation model, a modified culture condition that results in a calculated analysis value closest to the target value;
a second culturing step of culturing another culture cell belonging to a same cell line as the culture cell obtained in the sampling step under the modified culture condition, and sending a resulting culture to the analysis step and the analysis value calculation step;
a screening step,
wherein the steps from the sampling step to the second culturing step are repeatedly performed on different culture cells under different culture conditions,
wherein the screening step performs selecting and screening for a cell line and a culture condition related to the analysis values that are ±20% of the target value,
wherein culturing the different culture cells in the first culturing step and the second culturing step are simultaneously performed in a plurality of culture vessels,
wherein each of the plurality of culture vessels is respectively coupled to a medium feeder and a cell separator via a tube, and the cell separator is respectively coupled to a recovery vessel via a tube,
wherein each of the plurality of culture vessels controls the culturing by measuring a velocity of circulation of a culture medium from each of the plurality of culture vessels to each of the culture vessels via the cell separators, a velocity of delivery in which a solution is delivered from the cell separators to the recovery vessels, an adding rate in which fresh media from the medium feeders is added into each of the plurality of culture vessels, and a formulation of the fresh media, as a culture control parameter, and
wherein the correlation model correction step is performed between the analysis value calculation step and the culture condition computation step and corrects the correlation model based on the plurality of analysis values obtained in the analysis value calculation step.

2. The method according to claim 1,
wherein an isotope-labeled substrate is used in the first culturing step and the second culturing step to culture the culture cells.

3. The method according to claim 1,
wherein the steady state is determined based on at least one index selected from a nutrient substrate consumption rate of the cultured cell, a by-products secretory rate of the cultured cell, and a cell respiration rate of the cultured cell.

4. The method according to claim 1,
wherein the correlation model is constructed using a metabolic rate formula that takes a culture condition as a parameter.

* * * * *